(12) United States Patent
Schneider

(10) Patent No.: US 9,241,764 B2
(45) Date of Patent: Jan. 26, 2016

(54) METHOD OF MAKING POLYMERIC GLOVES HAVING EMBEDDED SURGICAL SUPPORT SYSTEMS AND DISCRETE ELEMENTS

(71) Applicant: Andrew I. Schneider, Palm Beach Gardens, FL (US)

(72) Inventor: Andrew I. Schneider, Palm Beach Gardens, FL (US)

( * ) Notice: Subject to any disclaimer, the term of this patent is extended or adjusted under 35 U.S.C. 154(b) by 665 days.

(21) Appl. No.: 13/626,771

(22) Filed: Sep. 25, 2012

(65) Prior Publication Data

US 2013/0117905 A1      May 16, 2013

Related U.S. Application Data

(60) Provisional application No. 61/539,350, filed on Sep. 26, 2011.

(51) Int. Cl.
| | |
|---|---|
| *A61B 19/04* | (2006.01) |
| *A61B 19/00* | (2006.01) |
| *A61B 17/00* | (2006.01) |
| *A61B 17/30* | (2006.01) |
| *A61B 17/32* | (2006.01) |
| *A61B 18/14* | (2006.01) |
| *A61B 18/00* | (2006.01) |

(52) U.S. Cl.
CPC ............... *A61B 19/04* (2013.01); *A61B 18/14* (2013.01); *A61B 19/5202* (2013.01); *A61B 2017/00438* (2013.01); *A61B 2017/306* (2013.01); *A61B 2017/320008* (2013.01); *A61B 2018/00595* (2013.01); *A61B 2217/005* (2013.01); *A61B 2217/007* (2013.01)

(58) Field of Classification Search
CPC ..... A41D 19/00; A41D 19/02; A63B 71/148; A63B 71/146; A61B 19/04
USPC ......... 2/159, 169, 161.1, 161.7, 161.3, 161.8, 2/163, 164
See application file for complete search history.

(56) References Cited

U.S. PATENT DOCUMENTS

| | | | |
|---|---|---|---|
| 2,311,276 A | 2/1943 | Wilcox | |
| 2,847,012 A | 8/1958 | Eastman | |
| 3,735,760 A | 5/1973 | Vreeland, Jr. | |
| 3,845,771 A | 11/1974 | Vise | |
| 3,875,945 A | 4/1975 | Friedman | |

(Continued)

FOREIGN PATENT DOCUMENTS

| | | |
|---|---|---|
| GB | 2316429 | 2/1998 |
| WO | 02/43550 A1 | 6/2002 |
| WO | 2010/085958 | 8/2010 |

*Primary Examiner* — Tejash Patel
(74) *Attorney, Agent, or Firm* — Duane Morris LLP; Gregory M. Lefkowitz

(57) ABSTRACT

A method of manufacturing a glove that includes discrete elements and component systems, such as, but not limited to, lights, electrical cautery, suction, and irrigation, attached to the surgical glove. The gloves produced by this method can be used as surgical gloves or for other industrial applications. In a particular application, the method includes providing a former comprising a hand-shaped portion and a first surgical system comprising a first surgical instrument, and a first switch for controlling the first surgical system. The former includes a first depression for receiving the first surgical system. The first depression is adapted to produce an interference fit with at least a portion of the first surgical system. The first surgical system can be loaded into the first depression and a polymer coating can be applied over the loaded former to form a surgical glove.

34 Claims, 20 Drawing Sheets

(56) References Cited

U.S. PATENT DOCUMENTS

| | | | | |
|---|---|---|---|---|
| 4,198,985 | A | 4/1980 | Abel | |
| 4,337,496 | A | 6/1982 | Laird | |
| 4,488,726 | A | 12/1984 | Murray | |
| 4,510,939 | A | 4/1985 | Brenman et al. | |
| 4,526,828 | A * | 7/1985 | Fogt et al. | 442/19 |
| 4,620,528 | A | 11/1986 | Arraval | |
| 4,779,290 | A * | 10/1988 | Welch et al. | 2/161.6 |
| 4,932,952 | A | 6/1990 | Wojciechowicz, Jr. | |
| 5,120,304 | A | 6/1992 | Sasaki | |
| 5,242,440 | A | 9/1993 | Shippert | |
| 5,255,167 | A | 10/1993 | Toussaint et al. | |
| 5,283,722 | A | 2/1994 | Koenen et al. | |
| 5,312,400 | A | 5/1994 | Bales et al. | |
| 5,535,105 | A * | 7/1996 | Koenen et al. | 362/570 |
| 5,632,548 | A * | 5/1997 | Mayfarth | 362/103 |
| 5,673,436 | A | 10/1997 | Piper | |
| 5,782,516 | A | 7/1998 | Partida | |
| 5,816,676 | A | 10/1998 | Koenen Myers et al. | |
| 5,911,848 | A * | 6/1999 | Haber et al. | 156/245 |
| 5,947,922 | A | 9/1999 | Macleod | |
| 6,112,330 | A | 9/2000 | Bryan | |
| 6,409,734 | B1 | 6/2002 | Zapata | |
| 6,551,312 | B2 | 4/2003 | Zhang et al. | |
| 6,567,990 | B1 | 5/2003 | Spitznagle | |
| 6,569,163 | B2 | 5/2003 | Hata et al. | |
| 6,592,235 | B1 | 7/2003 | Mayo | |
| 6,646,855 | B2 | 11/2003 | Buening et al. | |
| 6,711,746 | B1 * | 3/2004 | Orellana | 2/160 |
| 6,892,397 | B2 | 5/2005 | Raz et al. | |
| 7,012,797 | B1 | 3/2006 | Delida | |
| 7,503,667 | B2 * | 3/2009 | Wilkings | 362/103 |
| 7,814,570 | B2 * | 10/2010 | Hassan et al. | 2/161.1 |
| 7,931,648 | B2 * | 4/2011 | Schneider | 606/45 |
| 7,951,145 | B2 * | 5/2011 | Schneider | 606/45 |
| 8,182,479 | B2 * | 5/2012 | Schneider | 606/45 |
| 8,512,615 | B1 * | 8/2013 | Amdur et al. | 264/222 |
| 2003/0235048 | A1 | 12/2003 | Gyori | |
| 2004/0154071 | A1 | 8/2004 | Frahm | |
| 2004/0260281 | A1 | 12/2004 | Baxter et al. | |

\* cited by examiner

METHOD OF MAKING POLYMERIC GLOVES HAVING EMBEDDED SURGICAL SUPPORT SYSTEMS AND DISCRETE ELEMENTS

CROSS-REFERENCE TO RELATED APPLICATIONS

This application claims priority to U.S. Provisional Patent Application No. 61/539,350, entitled "Surgical Glove Systems and Methods of Making the Same," filed Sep. 26, 2011, the entirety of which is incorporated herein by reference.

FIELD OF THE INVENTION

This invention is directed generally to a method of manufacturing surgical gloves including integral surgical systems for use by a surgeon during surgery.

BACKGROUND

U.S. Pat. Nos. 7,931,648, 7,951,145 and 8,182,479 to Schneider ("Schneider Patents") disclosed surgical systems that include a glove with multiple surgical support systems attached thereto. Such gloves provide a number of advantages over conventional surgical systems where the gloves and surgical support systems (e.g., electrocautery, suction, irrigation, light, etc.) are not integrated. There are a wide variety of techniques useful for manufacturing conventional surgical gloves, which allow for high volume production of surgical gloves that meet stringent regulatory standards. However, these techniques are not sufficient for manufacturing the multi-functional surgical gloves described in the Schneider Patents, as they do not allow for the integral inclusion of embedded surgical support systems or other elements at the time of glove formation. Adapting commercial products to include surgical support systems would require post-formation processes that would not be cost effective and could compromise the gloves barrier properties. Therefore, there is a need for improvement in the techniques available in order to make and manufacture the surgical systems described in the Schneider Patents in a consistent, commercially reliable and cost-effective manner that will not compromise the surgical glove's material integrity or ability its to meet the required regulatory standards.

SUMMARY OF THE INVENTION

This invention relates to a method of making polymeric gloves, including surgical gloves or other industrial gloves, that contain embedded functional components. The method of making can include providing a first functional component, wherein the first functional component is selected from a first discrete element and a first component system coupled to a first conduit. The method can the include providing a former comprising an appendage-shaped portion, where the former includes a first depression for receiving the first functional component. The method can include loading the first functional component into the first depression; and applying a polymer coating over the loaded former to form an polymeric glove.

The first depression can be adapted to produce an interference fit with at least a portion of the first functional component. A portion of the first functional component can be embedded within the polymeric glove and another portion of the first functional component can be exposed.

The first functional component can be a first component system comprising a first active end and a first conduit, and the first depression can include a corresponding first active end receiving portion and a first conduit receiving portion. The loading step can include loading the first active end into the first active end receiving portion and the first conduit into the first conduit receiving portion. Exemplary active ends include light sources, cutting tips, suction tips, and irrigation tips. The first functional component is a first discrete element.

The method can also include providing a second functional component, where the second functional component is selected from a second discrete element and a second component system coupled to a second conduit. The former can also include a second depression for receiving the second functional component, and the method can include loading the second functional component into the second depression.

In a specific application, the method can include providing a first surgical system comprising a first surgical instrument and a first switch for controlling the first surgical system, and providing a former comprising a hand-shaped portion. The former can include a first depression for receiving the first surgical system, and the first depression can be adapted to produce an interference fit with at least a portion of the first surgical system. The first surgical system can be loaded into the first depression. A polymer coating can be applied over the loaded former then cured and/or dried to form a surgical glove with the surgical system integrated (e.g., partially or fully embedded) therein. The methods described herein can be used to make any of a variety of surgical gloves for use in the surgical systems described herein or in the Schneider Patents.

The first depression can include a first surgical instrument receiving portion and a first switch receiving portion. The first surgical system can also include a first conduit, and the first depression can include a first conduit receiving portion.

The interference fit can be formed with a portion of the first surgical instrument, a portion of the first switch, or both. The first surgical system can also include a proximal interconnection and the interference fit can be formed with a portion of one or more of the first surgical instrument, the first switch, and the proximal interconnection.

The former can include a wrist portion and a proximal forearm portion. The applying step can include dipping the loaded former into a pool of coating precursor. The method can also include removing the surgical glove from the former by turning the surgical glove inside-out once the coating precursor has stabilized, e.g., polymerized or cured, sufficiently to remove the glove without tearing. The coating precursor can produce a polymer coating that is sufficiently elastic after it's stabilized to enable the glove to be removed from the former without tearing.

A portion of the first surgical system can be embedded within the surgical glove and another portion of the first surgical system can be exposed. The exposed portion of the surgical instrument can include a portion of the first surgical instrument, a portion of the first switch, or a portion of both. The exposed portion can correspond to the portion of the first surgical system producing an interference fit with the first depression.

The method can also include providing a second surgical system that includes a second surgical instrument and a second switch for controlling the second surgical system. The former can also include a second depression for receiving the second surgical system, and the second depression can be adapted to produce a second interference fit with at least a portion of the second surgical system. The method can also include loading the second surgical system into the second depression.

The first depression can include a first surgical instrument receiving portion and a first switch receiving portion, while the second depression can include a second surgical instrument receiving portion and a second switch receiving portion. The first and second surgical systems can include first and second conduits, respectively. The first depression can include a first surgical instrument receiving portion, a first conduit receiving portion, and a first switch receiving portion, while the second depression can include a second surgical instrument receiving portion, a second conduit receiving portion, and a second switch receiving portion. The former can be designed so that the first and second conduit receiving portions do not intersect.

An interference fit can be formed between the first depression and a portion of the first surgical instrument, a portion of the first switch, or both, and a second interference fit can be formed between the second depression and a portion of the second surgical instrument, a portion of the second switch, or both.

The first and second surgical systems can also include first and second proximal interconnections, respectively. An interference fit can be formed with a portion of at least one of the first surgical instrument, the first switch and the first proximal interconnection, and a second interference fit can be formed with a portion of at least one of the second surgical instrument, the second switch and the second proximal interconnection.

A portion of the first surgical system can be embedded within the surgical glove and another portion of the first surgical system can be exposed. Similarly, a portion of the second surgical system can be embedded within the surgical glove and another portion of the second surgical system can be exposed. The exposed portion of the first surgical system can be a portion of the first surgical instrument, a portion of the first switch or both, and the exposed portion of the second surgical system can be a portion of the second surgical instrument, a portion of the second switch or both.

The former can also include a first discrete element depression. The first depression can include a first surgical instrument receiving portion, and the first discrete element depression and the first surgical instrument receiving portion can overlap. For example, where the first surgical instrument receiving portion is adapted to receive an electrocautery tip, the first discrete element depression can be adapted to receive a heat shield, which can be separate from or coupled to the electrocautery tip.

The method and former can be adapted for producing the surgical glove systems as described herein and in the Schneider Patents. Exemplary surgical gloves can include a first and second surgical system attached to the surgical glove, where the first surgical system comprises a first surgical instrument and a first conduit and the second surgical system comprises a second surgical instrument and a second conduit. Each of the first and second surgical systems can be attached to an index finger, a long finger, or a little finger of the surgical glove. A first switch can be attached to the surgical glove for controlling the first surgical system, and the first switch can be attached to a finger of the surgical glove to which the first surgical system is attached. A second switch can be attached to the surgical glove for controlling the second surgical system, and the second switch can be attached to a finger of the surgical glove to which the second surgical system is attached. The first and second switches can be operable by a thumb of a human hand wearing the surgical glove.

An advantage of this invention is that the method provides techniques for producing robust elastomeric gloves with surgical support systems embedded partially or fully therein.

Another advantage of the invention is that the method provides techniques for producing robust elastomeric gloves with surgical support systems integrated therein, where the gloves are liquid and biologically impermeable, safe for use in operating room conditions, and meet regulatory standards.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

FIG. 1B is a volar view of the same former loaded with surgical systems, while

DETAILED DESCRIPTION OF THE INVENTION

Figure 1A:
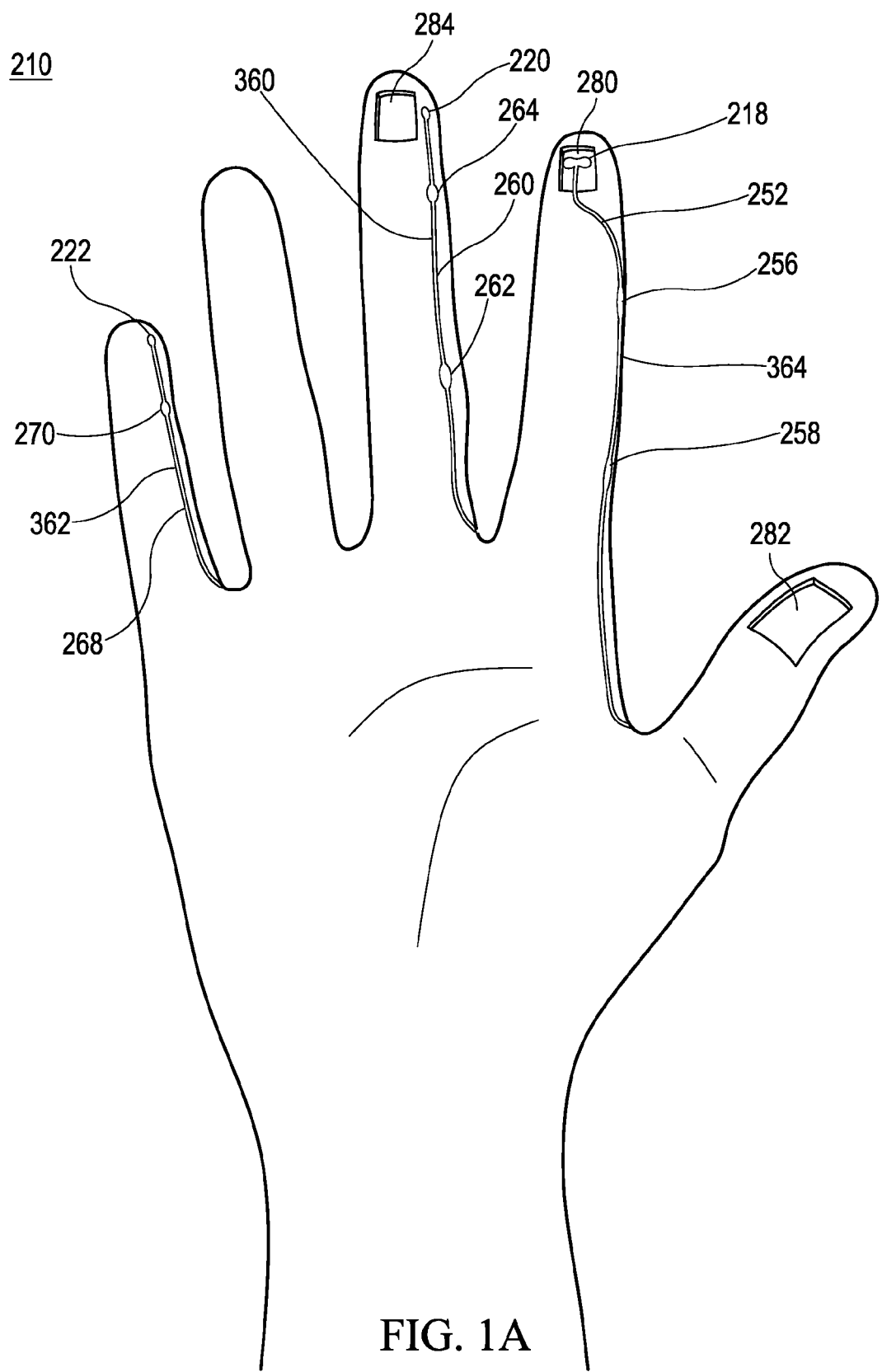
FIG. 1A is a volar view of a former for a surgical glove as described herein.

A method of making polymeric gloves with component systems, discrete elements, or both, embedded therein is described. The method can be used to completely or partially embed any of a variety of functional components (e.g., component systems, discrete elements) into a polymeric glove. The method of making polymeric gloves can be used to produce a wide variety of gloves including, but not limited to, surgical gloves, cleaning gloves, industrial gloves, and prophylactics. As used herein, "glove" is intended to have its conventional meaning and also include condoms, which can be made using the techniques described herein. Similarly, "appendage-shaped" is intended to include both hand-shaped and phallus-shaped objects.

As shown in the Figures, a method of making a polymeric glove can include providing a first functional component. The first functional component can be selected from a first discrete element and a first component system coupled to a first conduit. The method can also include providing a former comprising an appendage-shaped portion, where the former includes a first depression for receiving the first functional component. The method can include loading the first functional component into the first depression, and applying a polymer coating over the loaded former to form a polymeric glove. As described with respect to surgical gloves below, depending on the desired properties and configuration, the applying step can occur after the loading step or the applying step can occur both before and after the loading step.

As used herein, "functional component" is intended to include both component systems and discrete elements. As used herein, "component systems" include surgical and non-surgical functional components that includes a support conduit for physically connecting to a source (e.g., power source, suction source, irrigation source, etc.) external to the glove. Exemplary component systems include, but are not limited to, light sources 16, cutting sources 18, suction/vacuum sources 20, 554, and irrigation sources 22.

As used herein, "discrete element" refers to a functional component that does not include a conduit for physically connecting to a source external to the glove. Discrete elements must be adapted to functionally enhance the glove and do not include fillers or debris embedded within the material forming the glove. A discrete element could be non-physically connected to an external source, such as via a wireless connection, and could include an internal battery as a power supply. Exemplary discrete elements include, but are not limited to, insulating materials (e.g., heat shield), reinforcing elements, battery operated light sources, temperature strips, reflective elements, resistance thermometers, brushes and other cleaning implements, gripping and friction enhancing elements, and detection strips (e.g., pH, bacteria, toxin, etc.).

The first depression can be adapted to produce an interference fit with at least a portion of a first functional component. A portion of the first functional component can be embedded within the polymeric glove and another portion of the first functional component can be exposed.

The first functional component can be a first discrete element. The first discrete element—and any other discrete element described herein—can be a discrete element selected from the group consisting of insulating materials (e.g., heat shield), reinforcing elements, battery operated light sources, temperature strips, reflective elements, resistance thermometers, brushes and other cleaning implements, gripping and friction enhancing elements, and detection strips (e.g., pH, bacteria, toxin, etc.).

The first functional component can be a first component system comprising a first active end and a first conduit, and the first depression can include a first active end receiving portion and a first conduit receiving portion. In such methods, the loading step can include loading the first active end into the first active end receiving portion and the first conduit into the first conduit receiving portion.

The method can also include providing a second functional component. The second functional component can be selected from a second discrete element and a second component system coupled to a second conduit. The former can include a second depression for receiving a second functional component. The method can include loading the second functional component into the second depression. The first and second function components can be different or the same.

The method can be performed using at least two functional components, at least three functional components, at least four functional components, at least five functional components or more. Any combination of discrete elements and component systems can be used in the method.

Figure 9A:
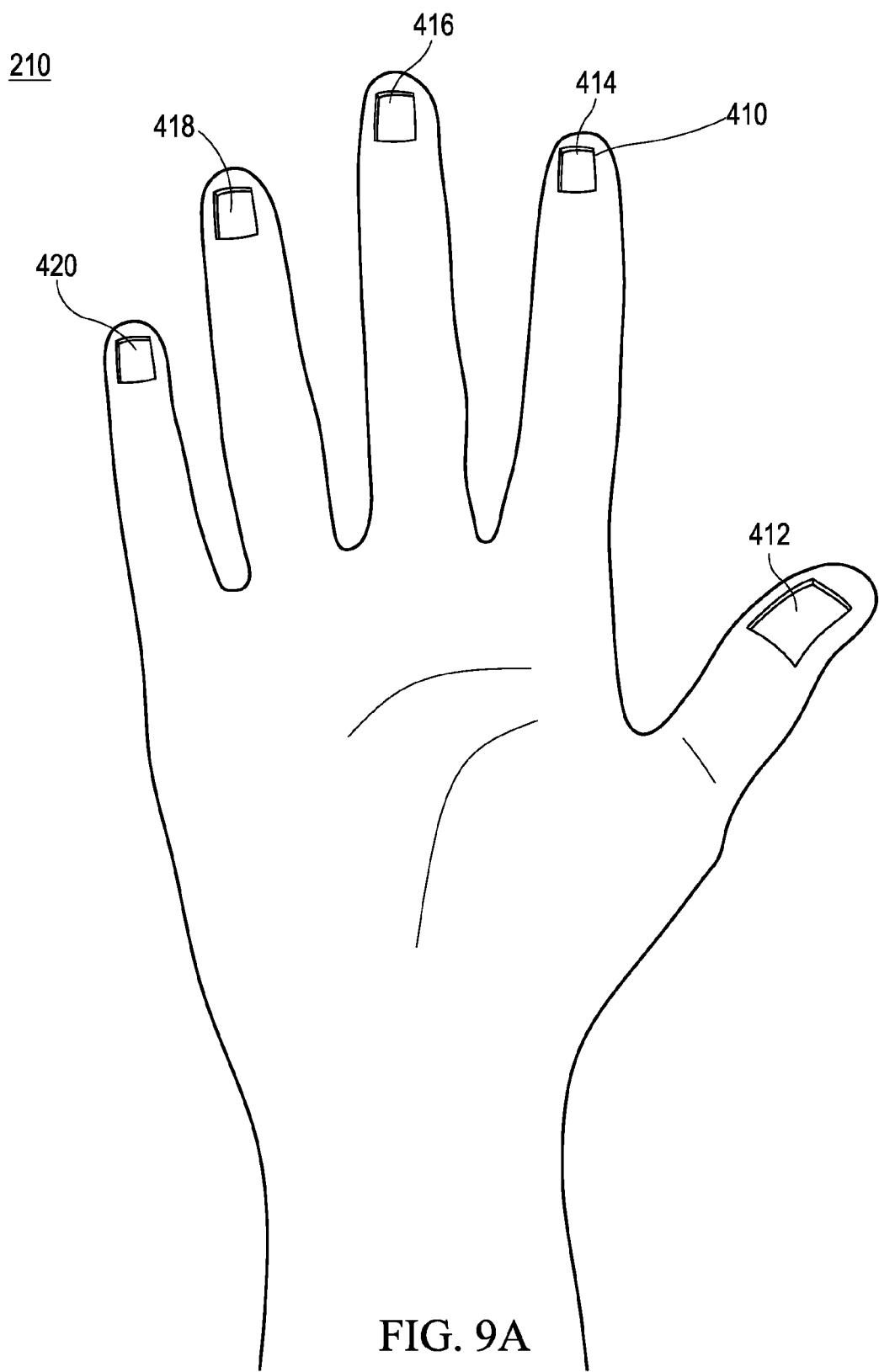
FIG. 9A is a volar view of a former for making a polymeric glove with discrete elements as described herein.
Figure 9B:
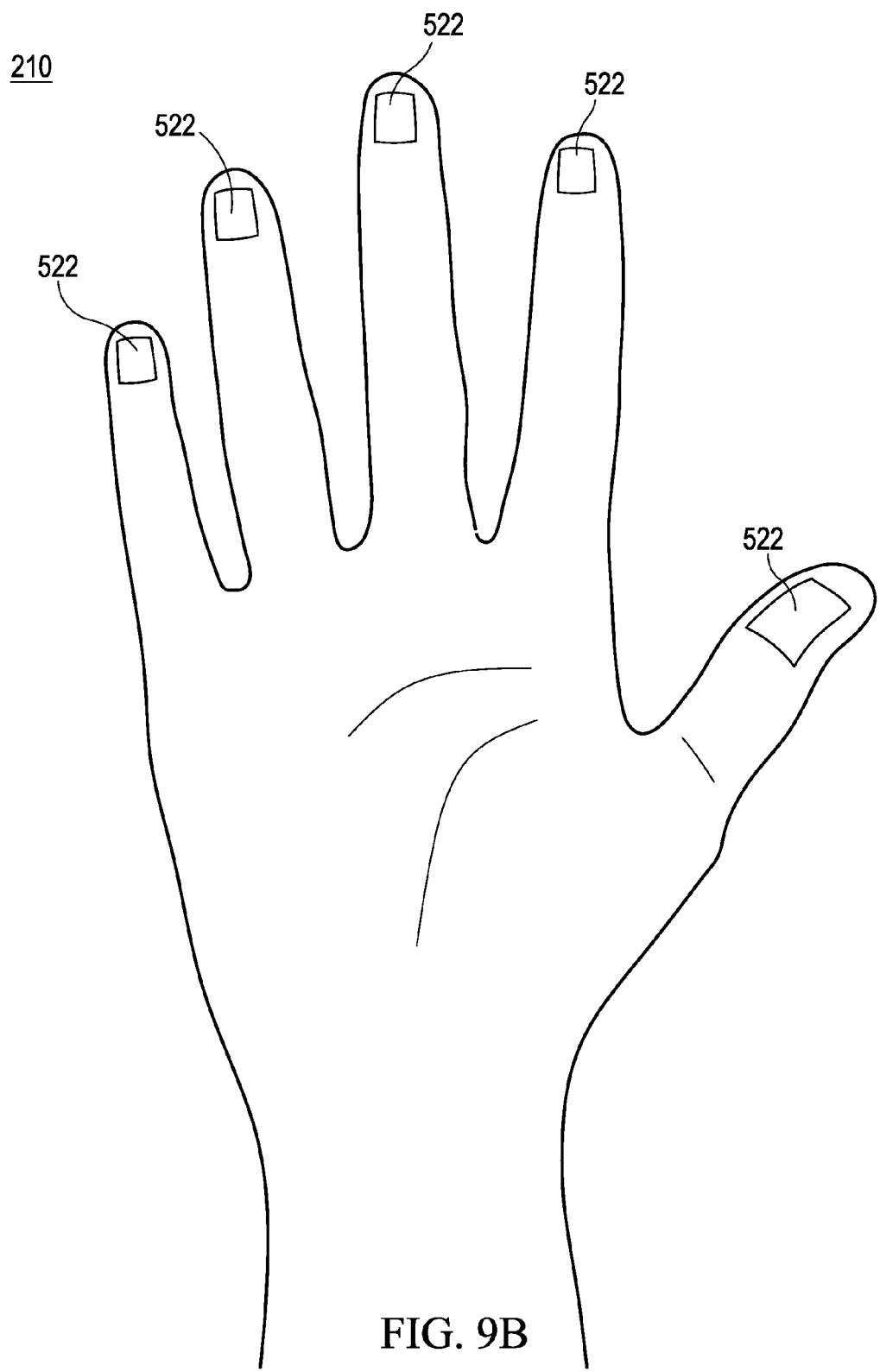
FIG. 9B is a volar view of the same former loaded with discrete elements.

As shown in FIG. 9, the former 210 can be adapted for producing a cleaning glove 512. FIG. 9A shows the former 210 in the unloaded state, while FIG. 9B shows the former 210 loaded with the discrete elements 522, 526.

In such a method, the former 210 can include discrete element receiving portions 410 at the distal, volar portion of the thumb 412 and each of the fingers 414, 416, 418, 420. The discrete element receiving portions 410 at the distal, volar portions of the thumb 412, index finger 414, long finger 416 and ring finger 418, respectively, can each be adapted to receive scrubbing elements 522. Exemplary scrubbing elements 422 include, but are not limited to, brushes, raised surfaces, undulating surfaces, and nubbed surfaces. The scrubbing surface 524 of the scrubbing elements 522 may be embedded in or protruding from the resulting glove 510, shown in FIG. 10.

The discrete element receiving portion 420 at the distal, volar portion of the little finger can be adapted to receive a detecting element 526, such as, a bacteria tester. The detecting element can be used to test for certain types of bacteria while the user is wearing the glove 512 formed using the former 210. The detection surface 528 can be embedded in or protruding from the glove 512 shown in FIG. 10. As will be understood, when it is desired for the discrete element 522, 526 to have an exposed surface (e.g., 524, 528), the discrete element receiving portions 410 can form an interference fit with the discrete element 522, 526.

Figure 10:
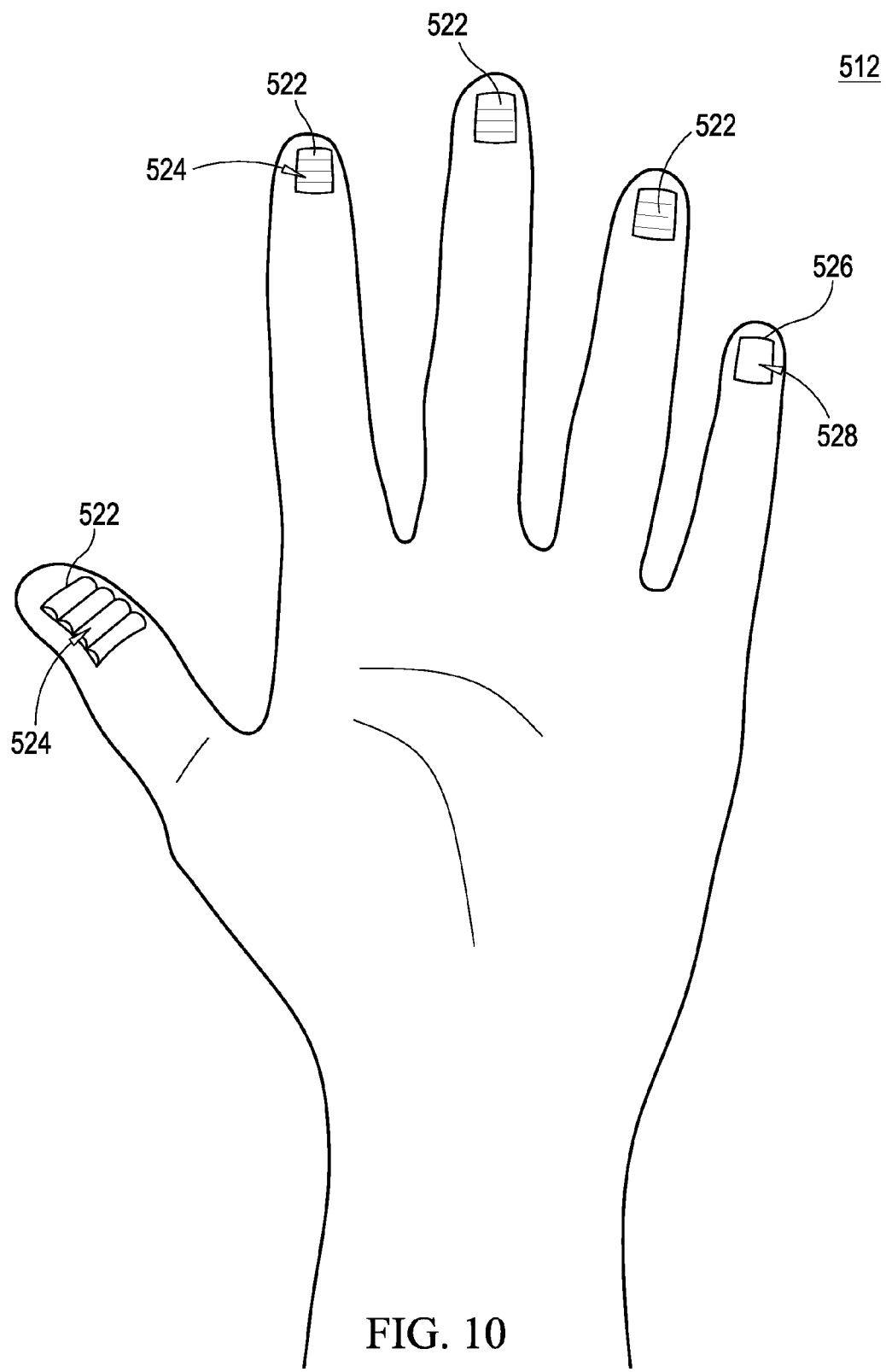
FIG. 10 is a volar view of a glove produced using the former of FIG. 9.

As shown in FIG. 10, the glove 512 can include scrubbing elements 522 at the distal, volar portions of the thumb, index finger, long finger and ring finger, and a detecting element 526 at the distal, volar portion of the little finger. In some gloves 512, for example when the scrubbing elements 522 are undulated surfaces, the scrubbing elements 522 can also facilitate gripping of objects. During the cleaning process, the user can monitor the detecting element 526 to determine if any undesirable bacteria or toxins are present. The detecting element 526 can be adapted to change appearance (e.g., color) if a target bacteria or toxin is present.

Figure 11A:
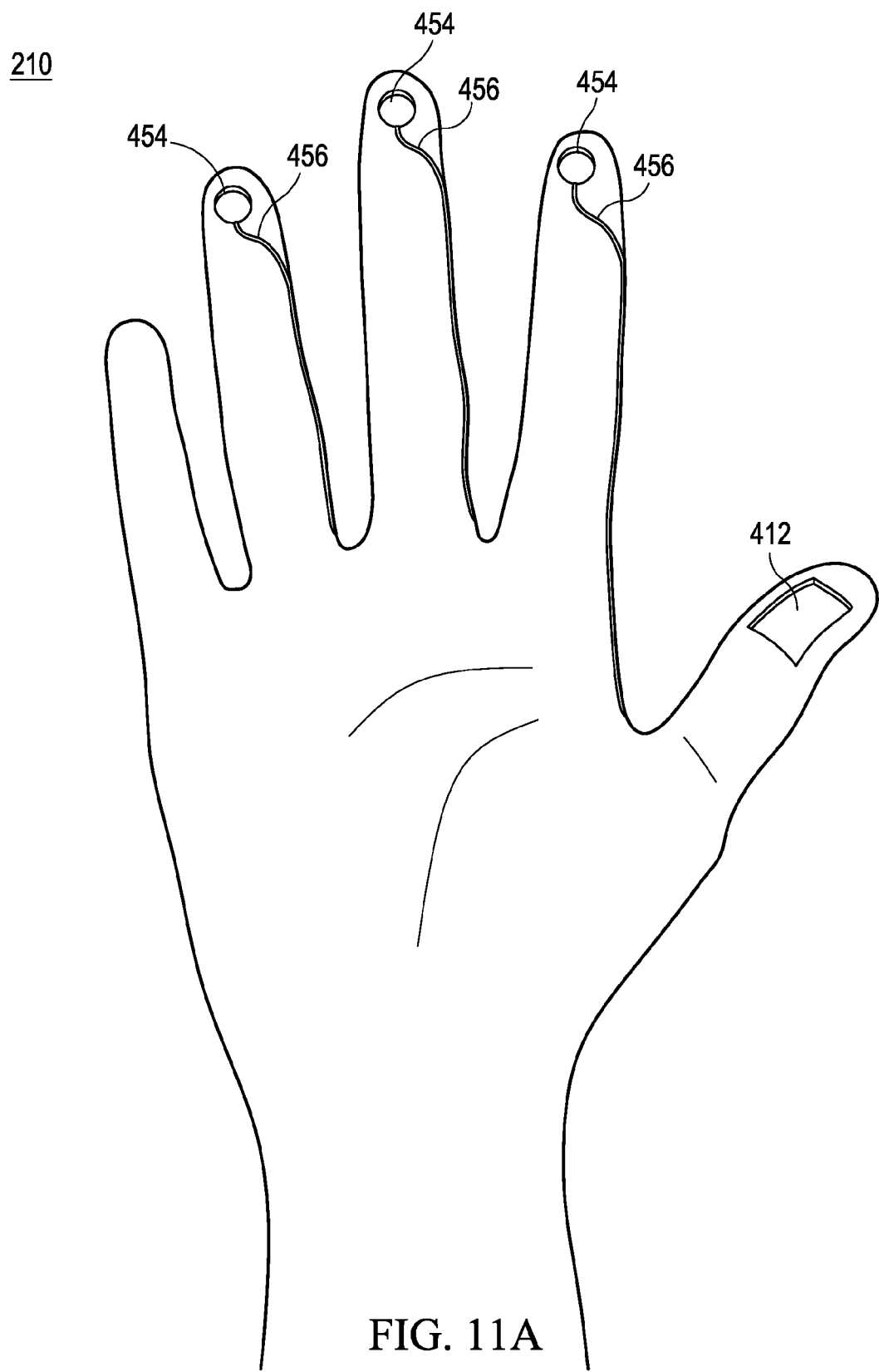
FIG. 11A is a volar view of a former for making a polymeric glove with discrete elements and component systems as, described herein.
Figure 11B:
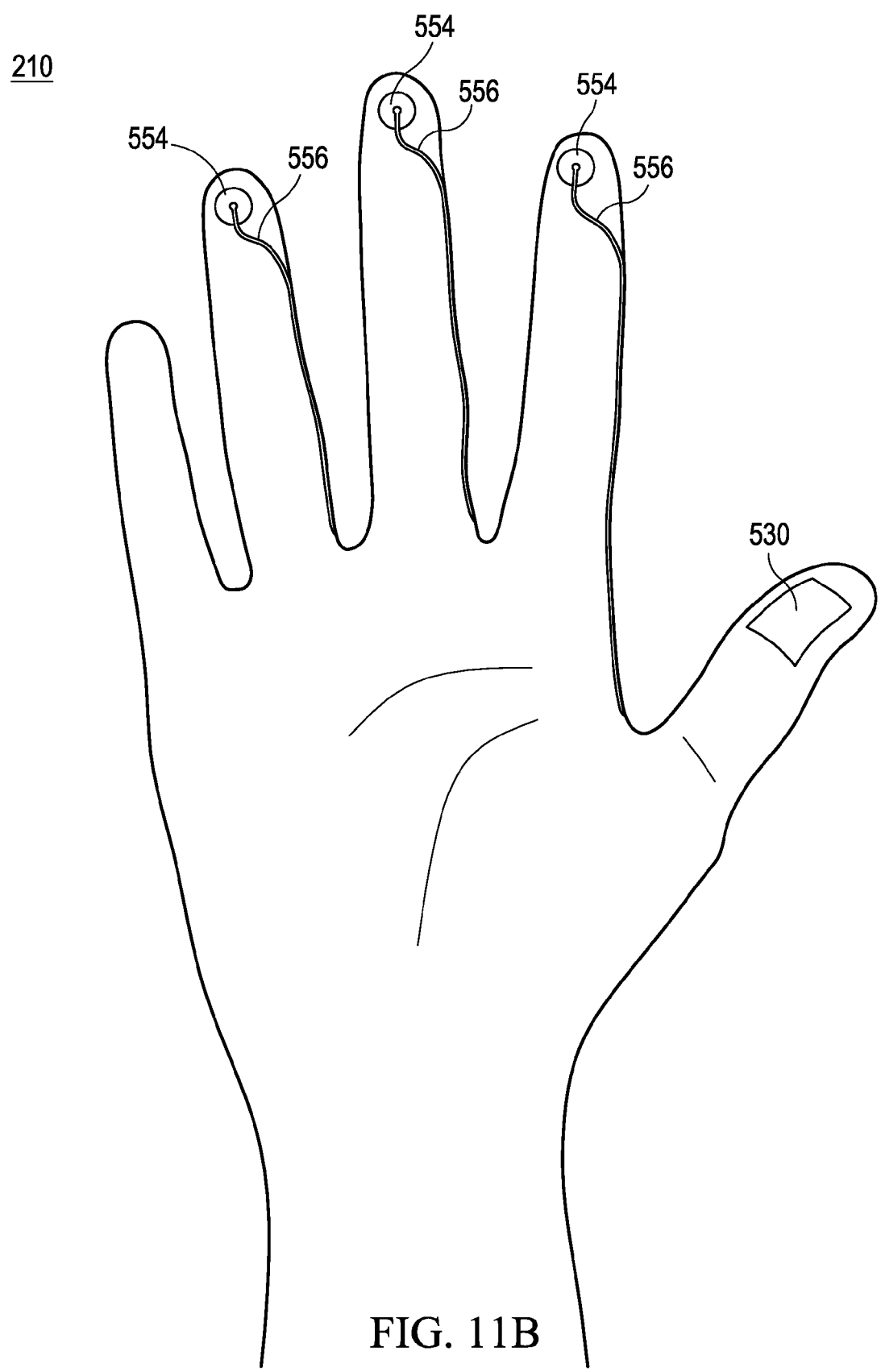
FIG. 11B is a volar view of the same former loaded with discrete elements and component systems.
Figure 12:
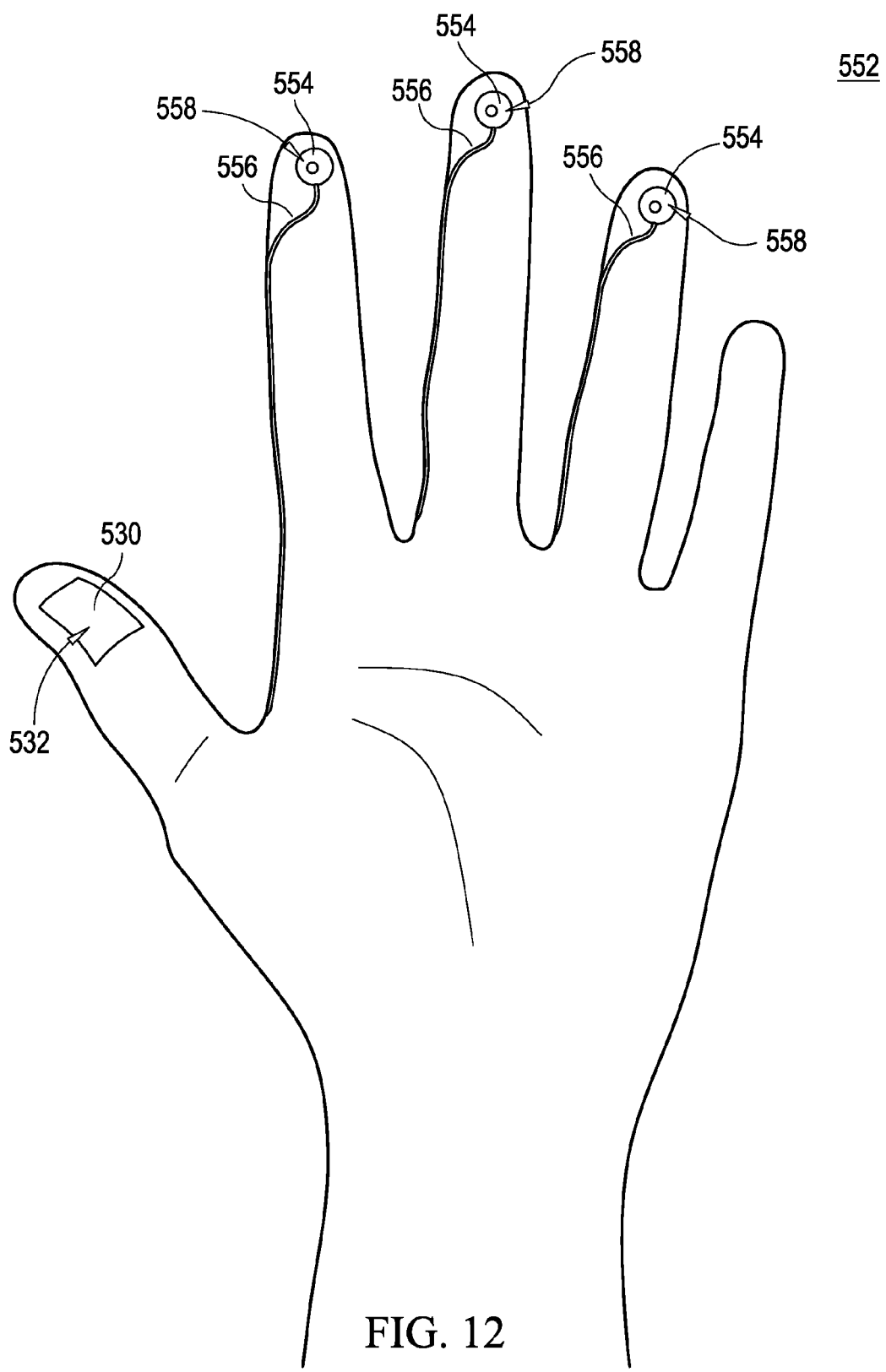
FIG. 12 is a volar view of a glove produced using the former of FIG. 11.

FIG. 11 shows a former 210 for producing the suction glove 552 shown in FIG. 12. The suction glove 552 can be adapted for handling delicate objects without introducing oils from the hand. For example, the suction glove 552 can be used to transport wafers or other objects in clean rooms.

As shown in FIG. 12, the glove 552 can include component systems comprising a vacuum cone 554 attached to distal, volar portions of the index finger, long finger and ring finger of the glove. Each of the vacuum cones 554 can be coupled to vacuum conduits 556 that extend along a radial aspect of the finger to which each vacuum cone 554 is attached and then over onto the dorsal aspect of the metacarpal of that finger before terminating at an interconnect in a manner analogous to the vacuum conduit 60 shown in FIG. 6. The vacuum conduits 4556 can be coupled to the vacuum cones 554 proximate an apex of the vacuum cones 554. The vacuum conduit 556 can also extend along an ulnar aspect of the finger to which it is attached in a manner analogous, but opposite, to that shown in FIG. 12. The glove 552 can also include a gripping element 530 on a volar surface of the thumb of the glove 552.

The inner surface 558 of the vacuum cone 554 can be protruding from the glove 552 and free from a coating of the polymer forming the body of the glove 552 (i.e., the inner surface 558 can be exposed). Similarly, the gripping surface 532 of the gripping element 530 can be exposed and/or protruding from the glove 552. As will be understood, when it is desired for a portion of the functional components 554, 530 to have a exposed surface (e.g., 532, 558) the corresponding receiving portions 412, 454 can form an interference fit with the functional components 554, 530.

Figure 2A:
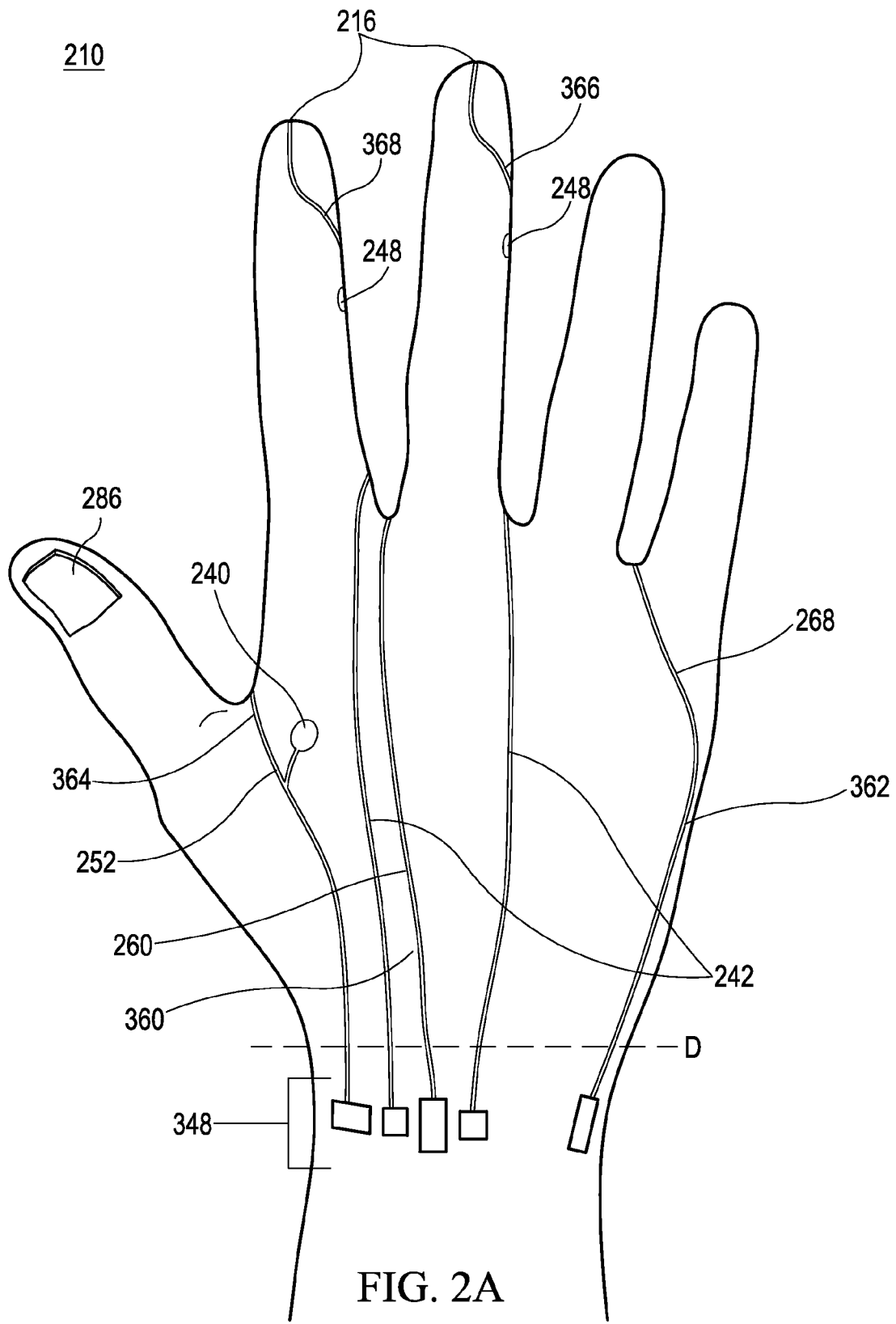
FIG. 2A is a dorsal view, of the former of FIG. 1.

FIG. 11A shows the former 210 in the unloaded state, while FIG. 11B shows the former 210 loaded with the vacuum systems 554, 556 and the gripping element 530. The vacuum cone receiving portions 454 are located at distal, volar portions of the index finger, long finger and ring fingers of the former 210. Vacuum conduit receiving portions 456 extend from the vacuum cone receiving portions 454 to a radial aspect of the finger on which each vacuum cone receiving portion 454 is located and then over onto a dorsal aspect of the metacarpal of that finger before terminating. The vacuum conduit receiving portion 456 can terminate in an interconnect receiving portion in a manner analogous to the suction conduit receiving portion 260 as shown in FIG. 2A. The thumb of the former 210 can also include a discrete element receiving portion 412, which can be loaded with a gripping element 530. The gripping element 530 can be useful for separating the component (e.g., a silicon wafer) being handled using the glove from the vacuum cones 554.

As a specific application of the method of making polymeric gloves, a method of making surgical gloves with surgical support systems embedded therein is also described. Although the following discussion is directed toward surgical gloves, surgical support systems, and surgical discrete elements, it should be understood that the techniques described herein can be used to embed any type of functional element into any polymeric glove or similar device. It should also be noted that the phrases "support system" and "component system" are used interchangeably herein.

The method can include providing an hand-shaped former 210 with a plurality of depressions, as shown in FIGS. 1A, 2A, 3A & 4A, and loading the depressions with corresponding surgical systems. A coating can be formed over and around the surgical systems by dipping the loaded former into a coating precursor solution one or more times. The method can include dipping the former into more than one coating precursor solution. The method can also include dipping the former into one or more coating precursor solutions—and, optionally, allowing the coating precursor to cure—prior to loading the former.

Prior to describing the method in more detail, exemplary gloves that can be made using the method will be described. The method described herein can be used to produce the gloves described in U.S. Pat. Nos. 7,931,648, 7,951,145 and 8,182,479 to Schneider, and U.S. patent application Ser. No. 13/626,733, entitled "Surgical Glove System, and Methods of Using the Same," filed Sep. 25, 2012, the entirety of which is incorporated herein by reference.

Figure 6:
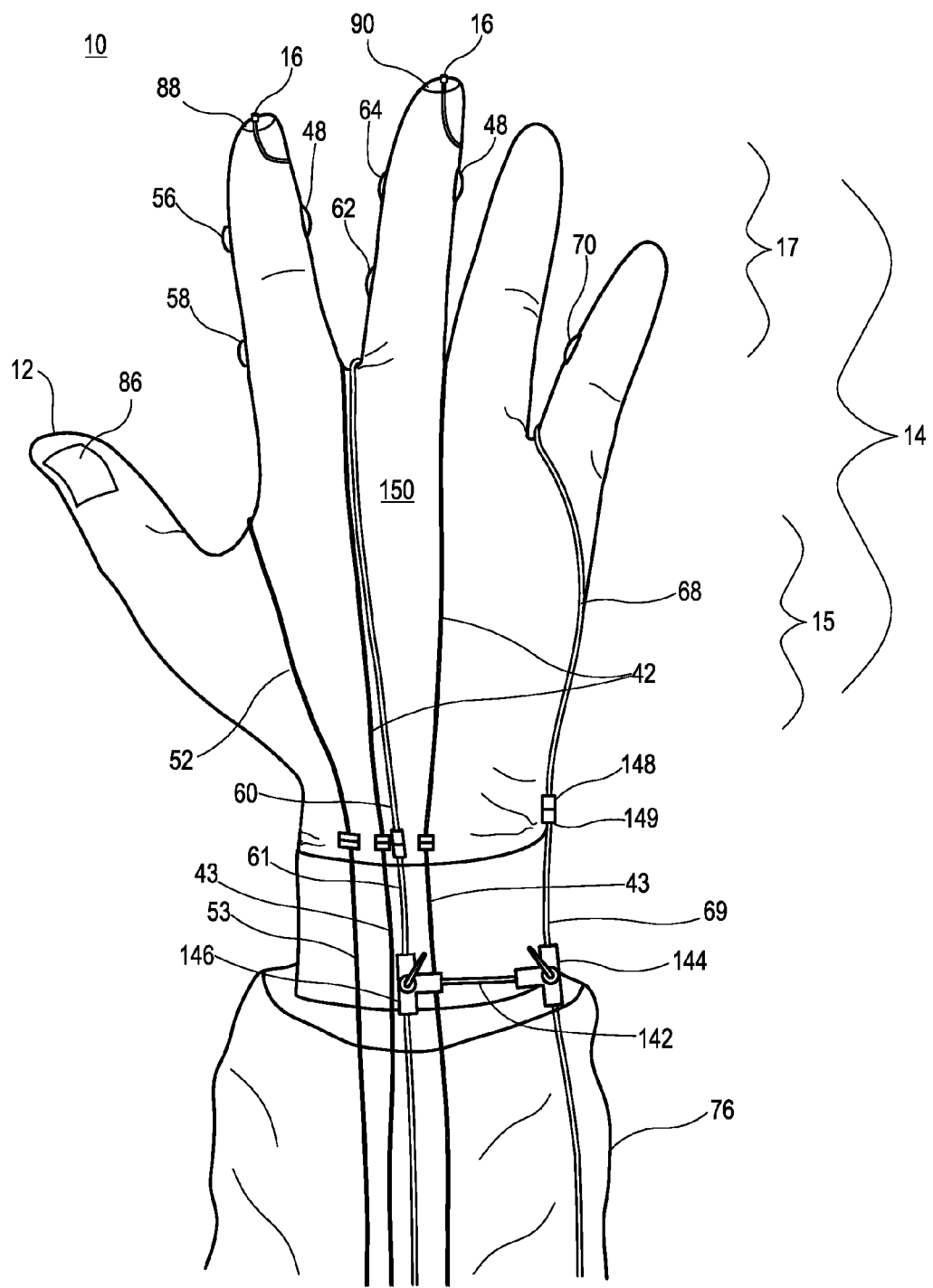
FIG. 6 is a dorsal view of a surgical system as described herein, including a right-handed glove and a shunt coupled to a sleeve of a surgical gown.
Figure 7:
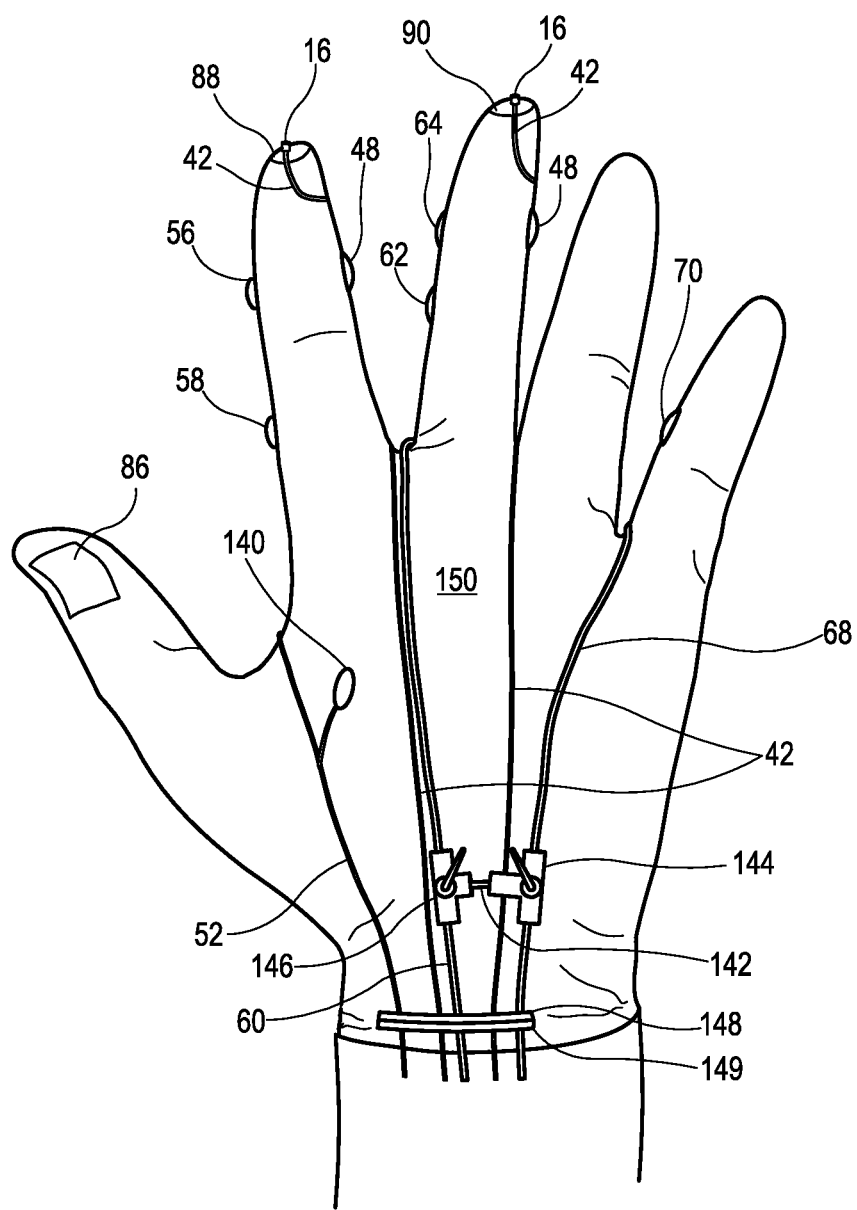
FIG. 7 is a dorsal view of a surgical system as described herein, including a right-handed glove with a shunt coupled thereto.
Figure 8:
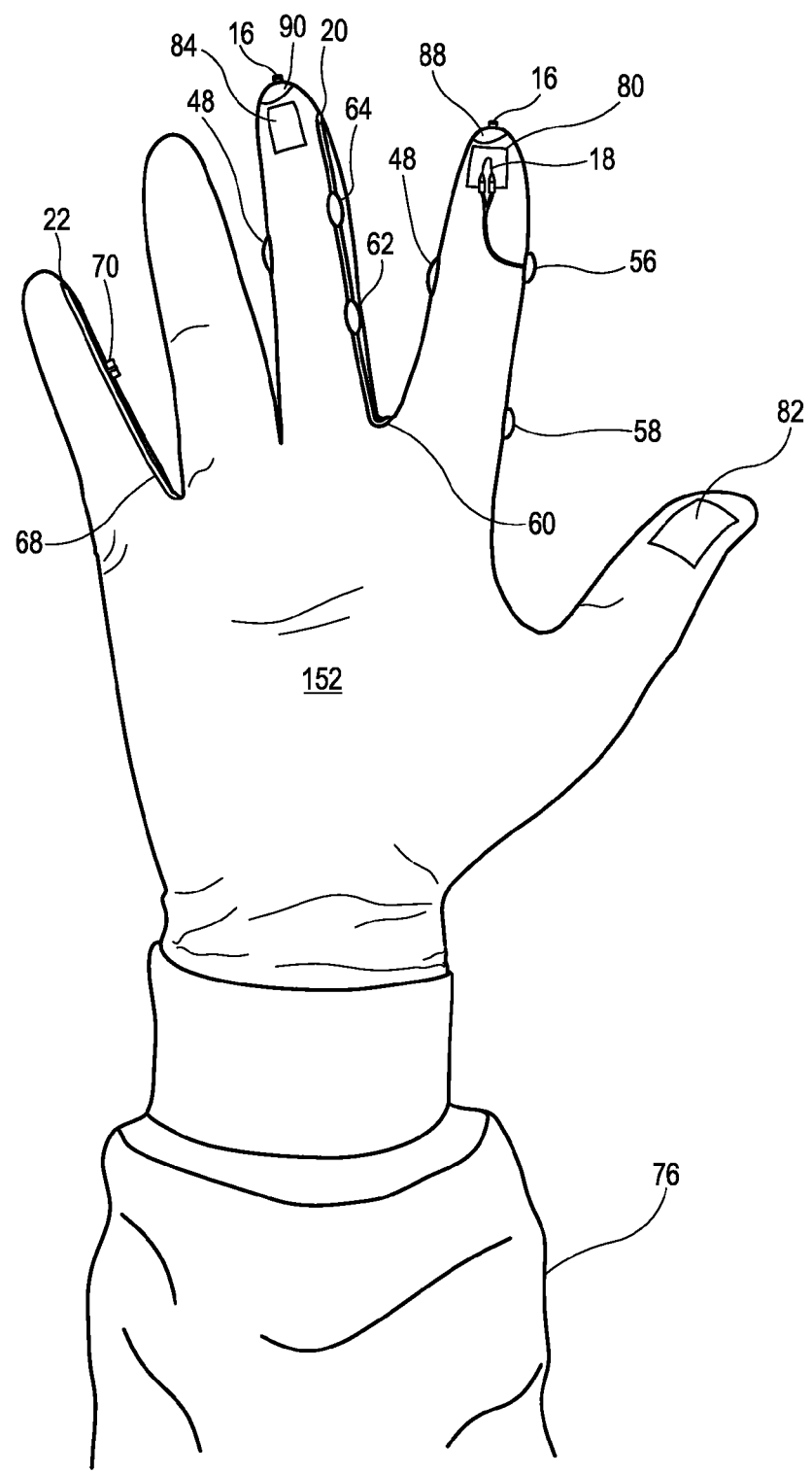
FIG. 8 is a volar view of the surgical system shown in FIGS. 6 and 7.

As shown in FIGS. 6-8, the surgical system 10 can include a surgical glove 12 configured to be removably attached to a human hand. The glove 12 can include first and second surgical systems 14 attached to the glove 12, wherein the first surgical system 14 comprises a first surgical instrument 17 and a first conduit 15, and the second surgical system 14 comprises a second surgical instrument 17 and a second conduit 15. Each of the first and second surgical systems 14 can be attached to an index finger, a long finger or a little finger of the surgical glove 12. Similarly, as shown in the Figures, the thumb and the ring finger of the surgical glove 12 can be free of all surgical systems 14.

The surgical systems 14 can also include a first and a second switch (e.g., 48, 56, 58, 62, 64, 70 and 140) attached to the glove 12 for controlling the first and second surgical systems 14, respectively. The first and second switches (e.g., 48, 56, 58, 62, 64, 70 and 140) can be attached to a finger of the glove 12 to which the first and second surgical systems 14 are attached, respectively. The first and second switches (e.g., 8, 56, 58, 62, 64, 70 and 140) can be operable by a thumb of a human hand wearing the glove 12.

The surgical systems 14 can also include (i) a safety switch 140 attached to the glove 12 for controlling the first surgical system 14 so that said first surgical system 14 will not operate unless both said first switch (e.g., 56 or 58) and the safety switch 140 are actuated simultaneously, or (ii) a shunt 142 for controlling fluid flow between said first and second conduits (e.g., 60 and 68). In some cases, the surgical system 14 can include one or more additional surgical systems 14 and can include both a safety switch 140 and a shunt 142.

The surgical system 10 can also include a surgical gown 30 that includes a support system comprising first and second support conduits 34 for coupling to the first and second conduits 15 of the surgical glove 12, respectively. The first and second support conduits 15 can be attached to the first sleeve of the gown 30 and can terminate is support connectors 149.

The first and second surgical systems 14 can include at least one irrigation port 22 and at least one suction port 20, respectively. The surgical system 10 can include a shunt 142 for controlling fluid flow between the irrigation conduit 68 and the suction conduit 60. The shunt 142 can be used to direct the flow of fluid from the irrigation conduit 68 to the suction conduit 60. The shunt 142 can also be used to direct the flow of fluid toward the suction port 22, away from the suction port 22, or both, either simultaneously or alternately. This can be particularly useful for clearing debris, such as tissue, from the suction system (22, 68 & 69).

The shunt 142 can include first and second T-valves 144, 146 in fluid communication with the irrigation conduit 68 and the suction conduit 60, respectively. The first T-valve 144 can be in fluid communication with the second T-valve 146. As shown in FIG. 6, a first portion of the shunt (e.g., 144) can be in-line with the irrigation support conduit 69 and a second portion of the shunt (e.g., 146) can be in-line with the suction support conduit 61. Alternately, as shown in FIG. 7, a first portion of the shunt (e.g., 144) can be in-line with the irrigation conduit 68 and a second portion of the shunt (e.g., 146) can be in-line with the suction conduit 60.

As shown in FIGS. 6-8, the surgical glove 12 can include light sources 16, an electrocautery device 18, a suction port 20, and an irrigation port 22 coupled to the same glove. A first light source 16 can be located on a distal portion of an index finger and a light conduit 42 can run along an ulnar portion of the index finger onto a dorsal portion 150 of the metacarpals (e.g., between the second and third metacarpals). A second light source 16 can be located on a distal portion of a long finger and a light conduit 42 can run along an ulnar portion of the long finger onto a dorsal portion 150 of the metacarpals (e.g., between the third and fourth metacarpals). The first and second light source control switches 48 can be attached to an ulnar portion of the finger of the glove to which the first and second light sources 16, respectively, are attached.

As shown in FIGS. 6-8, an electrocautery device 18 can be coupled to a distal or distal, volar 152 portion of the index finger. The electrocautery conduit 52 can run from the electrocautery device 18 along a radial portion of the index finger and then onto a dorsal portion 150 of the metacarpals (e.g., along a radial-dorsal portion of a second metacarpal). A cutting switch 56 and a coagulating switch 58 can be coupled to the electrocautery conduit 52 and positioned along a radial surface of the index finger such that the cutting and coagulating switches 56, 58 can be actuated by a thumb of the hand wearing the surgical glove 12. As used herein, "electrocautery device" is used broadly and is intended to include cutting sources such as electrical cautery sources, ultrasonic cutting surgical devices, and ultrasonic coagulating surgical devices.

As shown in FIG. 8, a heat shield 80 can be coupled to the glove and positioned between the user's hand and the electrocautery tip 18. This positioning can be adapted to prevent injury to the user and damage to the glove. The heat shield 80 can be separate from, or coupled to, the electrocautery tip 18.

As shown in FIG. 7, a safety switch 140 can be coupled to the electrocautery conduit 52 and positioned such that none of the fingers of the hand wearing the surgical glove 12 can actuate the safety switch 140. For example, the safety switch 140 can be positioned along a dorsal aspect 150 of the glove 12 covering the metacarpals of a hand wearing the glove. As shown in FIG. 7, the safety switch 140 can be attached to the surgical glove 12 proximate a dorso-radial aspect of a second metacarpal of a human hand wearing the surgical glove 12.

The electrocautery system can be designed such that the electrocautery device 18 cannot be activated unless both the safety switch 140 and the appropriate switch (56 or 58, respectively) are actuated simultaneously. Because of the positioning of the safety switch 140, activation of the electrocautery device 18 requires two hands and the potential for injury to the patient, the surgeon or other operating room personnel is greatly reduced or eliminated.

As shown in FIGS. 6-8, a suction port 20 can be coupled to a distal or distal, radial portion of the long finger. The suction conduit 60 can run from the suction port 20 along a radial aspect of the long finger and then onto a dorsal portion 150 of the metacarpals (e.g., along a dorsal portion between the second and third metacarpals). A suction port control switch 62 and a suction control port 64 can be provided along the suction conduit 60. The suction port control switch 62 and the suction control port 64 can be positioned along a radial surface of the long finger such that the suction port control switch 62 and the suction control port 64 can be actuated by a thumb of the hand to which the surgical glove 12 is attached.

As shown in FIGS. 6-8, an irrigation port 22 can be coupled to a distal or distal, radial portion of the lithe finger. The irrigation conduit 68 can run from the irrigation port 22 along a radial portion of the little finger and then onto a dorsal portion 150 of the metacarpals (e.g., along a dorsal portion on the radial or ulnar side of the fifth metacarpal). An irrigation control switch 70 can be provided along the irrigation conduit 68. The irrigation control switch 70 can be positioned along a radial surface of the little finger such that the irrigation control switch 70 can be actuated by a thumb of the hand to which the surgical glove 12 is attached.

Each of the conduits (42, 52, 60 and 68) can include a terminal interconnect 148 as a proximal end of the conduit. As shown in FIGS. 6 and 7, each of the terminal interconnects 148 can correspond to a support interconnect 149 located as a distal end of a corresponding support conduit (43, 53, 61 and 69). As shown in FIG. 7, the conduits (42, 52, 60 and 68) can terminate in a combined terminal interconnect 148 and the support conduits (43, 53, 61 and 69) can terminate in a combined support interconnect 149. The terminal interconnect(s) 148 can be a male or female interconnect and the support interconnect(s) 149 can be a complementary female or male interconnect.

Each of the conduits (42, 52, 60 and 68) can traverse a mid-coronal plane of a finger of the surgical glove 12. Similarly, each of the conduits (42, 52, 60 and 68) can follow a linear isometric path along a finger of the glove. This is of great benefit as it allows the manufacture of a snug fitting surgical glove with the conduits embedded therein. If, as in the prior art, the conduits are positioned along volar or dorsal surfaces of the glove, it is not possible to obtain the desired fit without increasing the risk of separation of the conduit from the glove.

Although FIGS. 6-8 are depicted with respect to a right-handed glove, it should be understood that any of the descriptions provided herein can apply equally to the left hand. To facilitate the description of left-handed gloves, the positioning of all aspects of the surgical system have been provided such that they are spatially unambiguous regardless of whether they refer to a right-handed glove or a left-handed glove. Of course, any and all of the surgical systems described herein can be attached to a right-handed glove or a left-handed glove. In some instances, the surgical system can include both a right-handed glove and a left-handed glove.

As shown in FIGS. 6-8, the surgical glove can also include additional discrete elements. The additional discrete elements can be embedded in the surgical glove. As will be understood, discrete elements generally refer to devices or objects attached to (embedded in) the surgical glove that do not include a conduit terminating in a terminal interconnect 148 (e.g., does not require a support conduit). Exemplary, discrete elements include, but are not limited to, a heat shield, a reinforcing element, a battery operated light source, a temperature strip, a reflective element, and a resistance thermometer.

FIGS. 6-8 show reinforcing elements 82 and 86 on the distal volar and distal dorsal portions of the thumb, respectively. The reinforcing elements (e.g., a mesh) can be designed to prevent tears to the glove when the thumb actuates the various switches (e.g., 48, 65, 58, 62, 64 and 70) or is used to manipulate or grasp other instruments.

In addition, discrete element 84 is positioned on a distal, volar portion of the long finger. This discrete element 84 can provide a reinforcing function or can provide an independent function, such as being a resistance thermometer, a reflector, or a temperature strip.

Reflective elements 88, 90 can be positioned proximate the light sources 16. As shown in FIGS. 6.8, the reflective elements 88, 90 can be positioned at distal ends of the index and long fingers, respectively. The reflective elements 88, 90 can be adapted for directing light emitted from the light sources 16 in a volar, distal direction. This enables the user to better illuminate the target, e.g., surgical field. Each reflective element 88, 90 can be separate from or coupled to the light source 16. The reflective elements 88, 90 can also be produced of a material adapted to insulate the user's hand and/or the glove from the heat radiating from the lights source 16 (e.g., halogen light).

It should be noted that, because the discrete elements (e.g., 80, 82, 84, 86, 88 & 90) can be thin, uniform sheets, the discrete elements can be included on any portion of the hand or any of the fingers, including the thumb and/or ring finger, without interfering with the surgeon's ability to manipulate surgical clamps or other surgical devices while wearing the surgical gloves. Alternately, the thumb and/or ring finger of the gloves can be free of both surgical systems and discrete elements.

Having described exemplary surgical gloves that can be made using the method described herein, a method of making surgical gloves such as those shown in FIGS. 6-8 is disclosed.

The method can include providing an hand-shaped former 210 with a plurality of depressions and loading the depressions with corresponding surgical systems. A coating can be formed over and around the surgical systems by dipping the loaded former into a coating precursor solution one or more times. The method can include dipping the former in to more than one coating precursor solution FIGS. 1-4 show exemplary formers 210 both with and without surgical systems 14.

As used herein, "depression" refers to an indentation for receiving a portion of a surgical system. Depressions—especially those for surgical systems—can include channel portions with generally U-shaped or V-shaped cross-sections having opposing sides that are generally parallel to one another. As used herein, "generally" refers to the general appearance of a cross-section or a minor deviation for a referenced orientation. For example, generally parallel sides deviate from parallel by ≤30°, or ≤20°, or ≤10°, or ≤5°. The sides of the depressions 214 described herein can have generally parallel sides where they are designed to form an interference fit with a portion of a surgical system 14. This helps enable the opposing sides of the former to for a liquid tight seal with the sides of the portion of the surgical system 14. It should be observed that where the cross-section is taken through the center of a depression that is circular, elliptical or similarly shaped, the sides of that shape can be considered generally parallel.

The method can include providing a first surgical system 14 comprising a first surgical instrument 17 and a first switch (e.g., 48, 56, 58, 62, 64, 70 & 140) for controlling the first surgical system 14. The method can include providing a former 210 comprising an hand-shaped portion 212. The former 210 can include a first depression 214 for receiving the first surgical system 14. The first depression 214 can be adapted to produce an interference fit with at least a portion of the first surgical system 14. The first surgical system 14 can be loaded into the first depression 214 and a polymer coating can be applied over the loaded former 210 to form a surgical glove 12. In addition to the hand-shaped portion, the former 210 can include a wrist portion and a proximal forearm portion.

The method can also include providing at least one discrete element (e.g., 80, 82, 84, 88) such as, but not limited to, a heat shield, a reinforcing material and a temperature indicating device. The former 210 can include at least one discrete element depression (e.g., 280, 282, 284, 288, 290) for receiving the at least one discrete element (e.g., 80, 82, 84, 86, 88, 90). The at least one discrete element depression (e.g., 280, 282, 284, 286, 288, 290) can be, but is not necessarily, adapted to produce an interference fit with at least a portion of the discrete element (e.g., 80, 82, 84, 86, 88, 90). The at least one discrete element can be loaded into the at least one discrete element depression (e.g., 280, 282, 284, 286, 288, 290) and a polymer coating can be applied over the loaded former 210 to form a surgical glove 12 using the methods described herein.

The applying step can include dipping the loaded former 210 into a pool of coating precursor. The applying step can include dipping the loaded former 210 into a pool of coating precursor more than once. The applying step can include dipping the loaded former 210 into more than one pool of coating precursor. For example, the loaded former 210 can be dipped into a polymer precursor and then into a polymer stabilization pool (e.g., cross-linker, catalyst, initiator, etc.). The method can be continuous. The method can include heating the loaded former 210 prior to dipping in order to facilitate formation of a coating on the loaded former 210.

As used herein, "coating precursor" is intended to include a composition helpful for forming a stabilized coating. Exemplary coating precursors include, but are not limited to, polymer precursors (e.g., monomer solutions), polymer solutions (e.g., latex solutions), catalysts, initiators, cross-linkers and mixtures thereof.

As used herein, "interference fit" is intended to refer to a seal that is fluid tight with respect to the coating precursor. In other words, former-side portions of features of a surgical system that form an interference fit with the former 210 will not be coated during the forming process and will be exposed (i.e., uncoated) once the glove 12 is removed from the former 210. In contrast, because the loaded former 210 is dipped in the coating precursor, all other portions of the surgical system 14 will be surrounded by (i.e., embedded within) the glove material.

The first depression 214 can include a first surgical instrument receiving portion 217 and a first switch receiving portion (e.g., 248, 256, 258, 262, 264 & 270). The first surgical system 14 can also include a first conduit 15 and the first depression 214 can also include a first conduit receiving portion 215. The first surgical system 14 can also include a proximal interconnection 148 and the first depression 214 can also include a proximal interconnection receiving portion 348. The interference fit can be formed with a portion of the first surgical instrument 17, a portion of the first switch (e.g., 48, 56, 58, 62, 64, 70 & 140), a portion of the proximal interconnection 148, or a combination thereof. In some formers 210, there will not be an interference fit between the conduit 15 and the first conduit receiving portion 215.

The method can also include removing the surgical glove 12 from the former 210 by turning the surgical glove 12 inside-out. A portion of the first surgical system 14 can be embedded within the surgical glove 12 and a portion of the first surgical system 14 can be exposed (i.e., extend from the surgical glove 12). The exposed portion can include a portion of the first surgical instrument, a portion of the first switch, or both. The exposed portion can correspond to the former-side of the portion of the first surgical system 14 producing an interference fit with the first depression 214.

As will be understood, it may be particularly useful to have particular portions of the surgical system 14 exposed. Portions that can be beneficial to expose include, but are not limited to, surgical instruments 17, switches (e.g., 48, 56, 58, 62, 64, 70 & 140), ports, and terminal interconnections 148. This may be particularly useful for providing access to switches and ports, as well as, for embodiments where the surgical instruments are removable. In such embodiments, the removable portion cab be attached to the glove after the forming process. In some methods, the former 210 may be dipped, fingers first, into the coating precursor pool to a depth such that the terminal interconnections do not contact the pool of coating precursor.

The method can also include providing a second surgical system 14 comprising a second surgical instrument 17 and a second switch (e.g., 48, 56, 58, 62, 64, 70 & 140) for controlling the second surgical system 14. The former 210 can also include a second depression 214 for receiving the second surgical system 14. The second depression 214 can be adapted to produce an interference fit with at least a portion of the second surgical system 14. The second surgical system 14 can be loaded into the second depression 214.

The second depression 214 can include a second surgical instrument receiving portion 217 and a second switch receiving portion 215. The second surgical system 14 can also include a second conduit 15 and the second depression 214 can include a second conduit receiving portion 215. The second surgical system 14 can also include a proximal interconnection 148 and the second depression 214 can include a proximal interconnection receiving portion 348. The interference fit can be formed with a portion of the second surgical instrument 17, a portion of the second switch (e.g., 48, 56, 58, 62, 64, 70 & 140), a portion of the proximal interconnection 148, or a combination thereof. In some formers 210, there will not be an interference fit between the second conduit 15 and the second conduit receiving portion 215.

As will be understood, additional surgical systems 14 and depressions 214 can be included in order to produce any and all embodiments of surgical gloves 12 described herein. For example, the depressions 214 for receiving the surgical systems 14 can be positioned in an index finger, a long finger or a lithe finger of the former 210. Similarly, as shown in FIGS. 1-4, the thumb and the ring finger of the former 210 can be free of all depressions for receiving surgical systems 214. In some formers 210, the multiple depressions 214 do not intersect with one another in order to facilitate uniform coating of the surgical systems 214.

Depending of the desired configuration, the some or all of the surgical systems 14 and discrete elements (e.g., 80, 82, 84, 86, 88, 90) can be loaded into the respective depressions 214 before or after the former 210 is dipped into the first coating precursor material. Where the surgical system(s) 14 and/or discrete elements (e.g., 80, 82, 84, 86, 88, 90) are loaded into the respective depressions after the former 210 is dipped into the coating precursor material, the former 210 will generally also be dipped into the coating precursor material after the surgical systems 14 and/or discrete elements (e.g., 80, 82, 84, 86, 88, 90) are loaded into the former 210.

When the surgical system(s) 14 and/or discrete elements (e.g., 80, 82, 84, 86, 89, 90) are intended to be completely embedded in the glove, the method may be performed so that the former 210 is dipped both before and after the surgical system(s) 14 is/are loaded into the depressions 214 of the former 210. In such methods, the former 210 may be dipped more than once before the surgical system(s) 14 is/are loaded 210 and more than once after the surgical system(s) 14 is/are loaded into the former 210. For example, they former may be dipped into a polymer precursor (e.g., monomer solutions) or polymer solution (e.g., latex solutions) and subsequently dipped into a solution containing one or more of a catalyst, an initiators and a cross-linker.

FIGS. 1-4 depict a former 210 that can be used to make a glove that is the mirror image of the glove shown in FIG. 6. In FIGS. 1-4, the A series (FIGS. 1A, 2A, 3A & 4A) shows various perspectives of the former 210 and the empty depressions 214 therein, while the B series (FIGS. 1B, 2B, 3B & 4B) shows those same perspectives of the former 210 where the depressions 214 are loaded with the surgical systems 14 and, in the case of 2B, discrete elements. FIGS. 1C and 4C show the volar perspective of the former 210 loaded with both surgical systems 14 and discrete elements.

FIGS. 1-4 show various views of a former 210 used to form a left-handed glove. The former 210 can include a suction system depression 360. As shown in the volar view of FIG. 1, the suction system depression 360 can include a suction device receiving portion 220, a suction port control switch receiving portion 262, a suction control port receiving portion 264, and a suction conduit receiving portion 260. As shown in FIG. 2, the suction system depression 360 can include a terminal connector receiving portion 348 proximate a wrist portion of the former 210. The suction system depression 360 can start proximate a distal end of the long finger and extend along volar aspects, radial aspects or volar-radial aspects of the long finger. As shown in FIG. 2, the suction system depression 360 can then continue to a dorsal side of the former 210 between the long finger and the index finger of the former and extend between or proximate the second and third metacarpals.

Figure 5A:
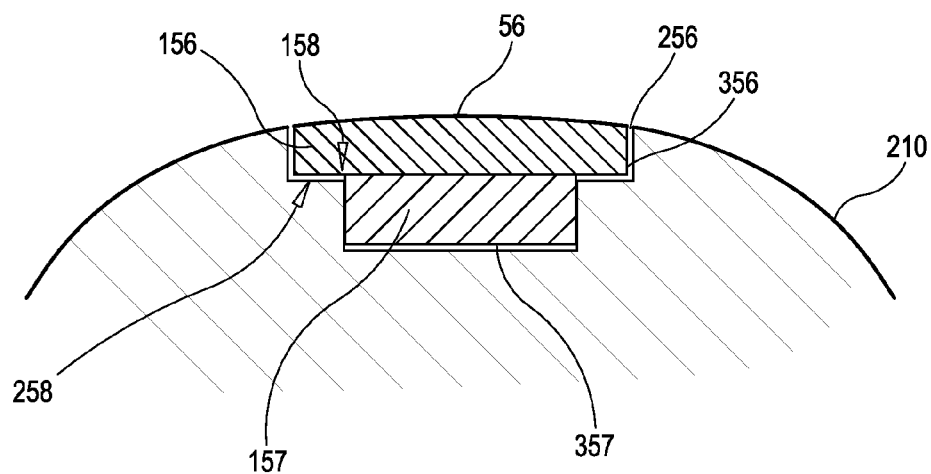
FIG. 5A is a cross-sectional view of an interference fit with the cutting switch taken along outline 5A-5A of FIG. 3B.
Figure 5B:
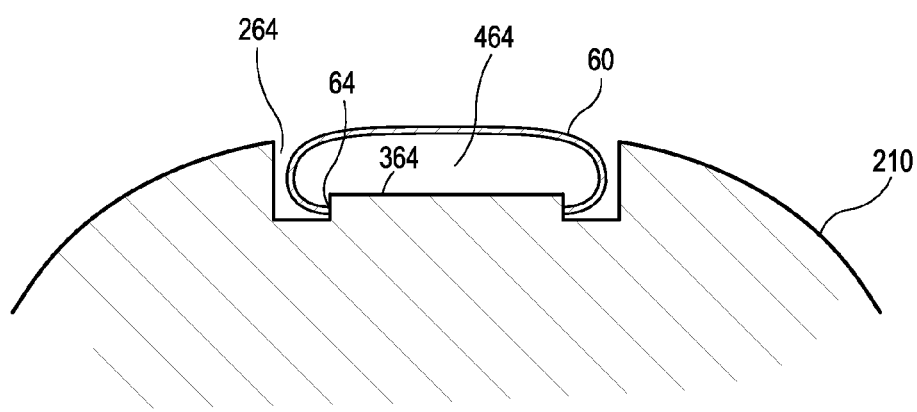
FIG. 5B is a cross-sectional view of an interference fit with the suction control port taken along outline 5B-5B of FIG. 3B.

An exemplary interference fit for the suction control port 64 is shown in FIG. 5B. The suction control port 64 can be an opening in the suction conduit 60. As shown in FIG. 5B, suction control port receiving portion 264 can include a suction control port projection 364 adapted for plugging the suction control port 64. The fit between the sides of the suction control port 64 and the suction control port projection 364 can be sufficient to prevent coating precursor from flowing between the sides and into the lumen 464 of the suction conduit 60.

Figure 1B:
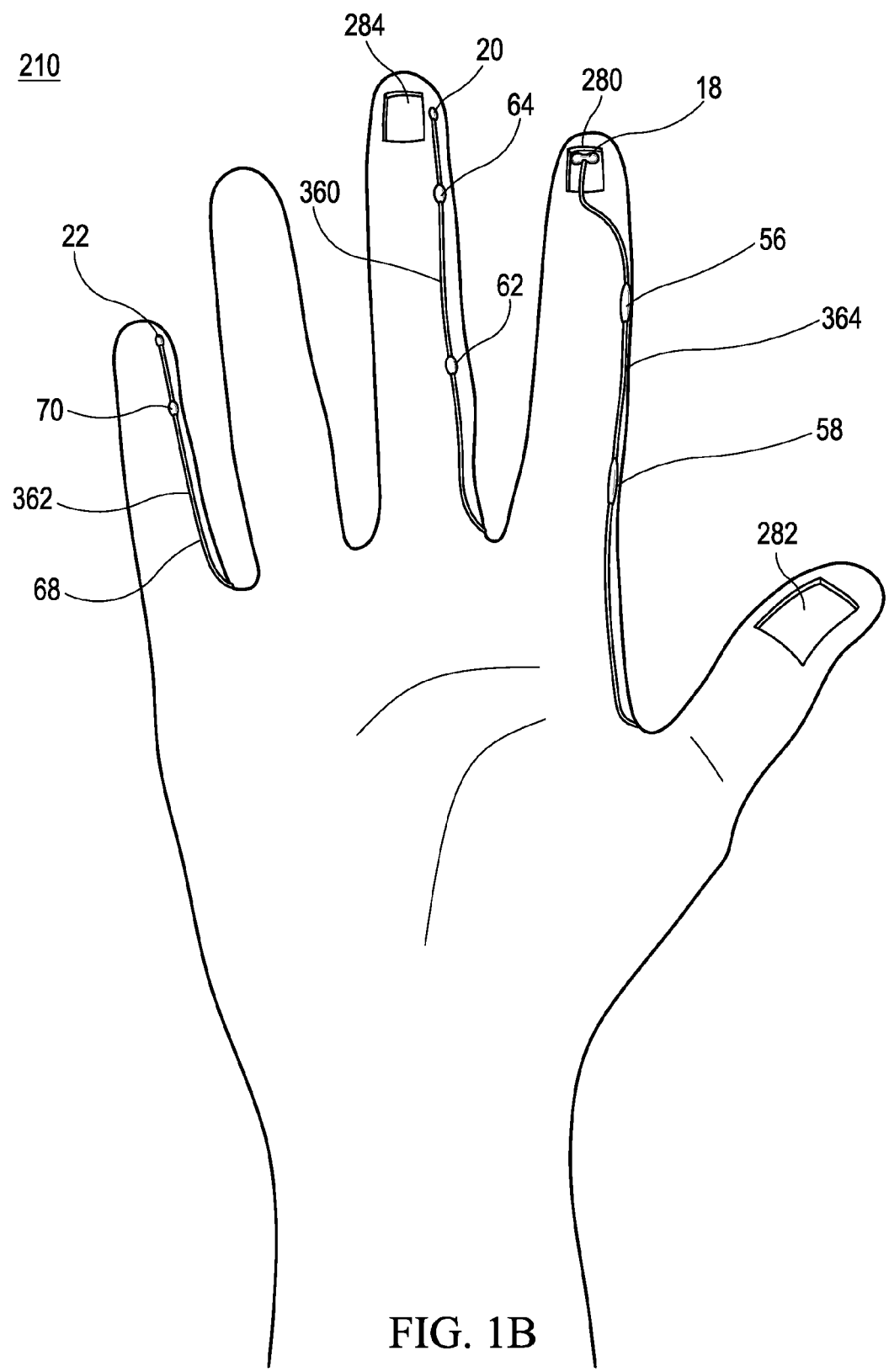
Figure 1C:
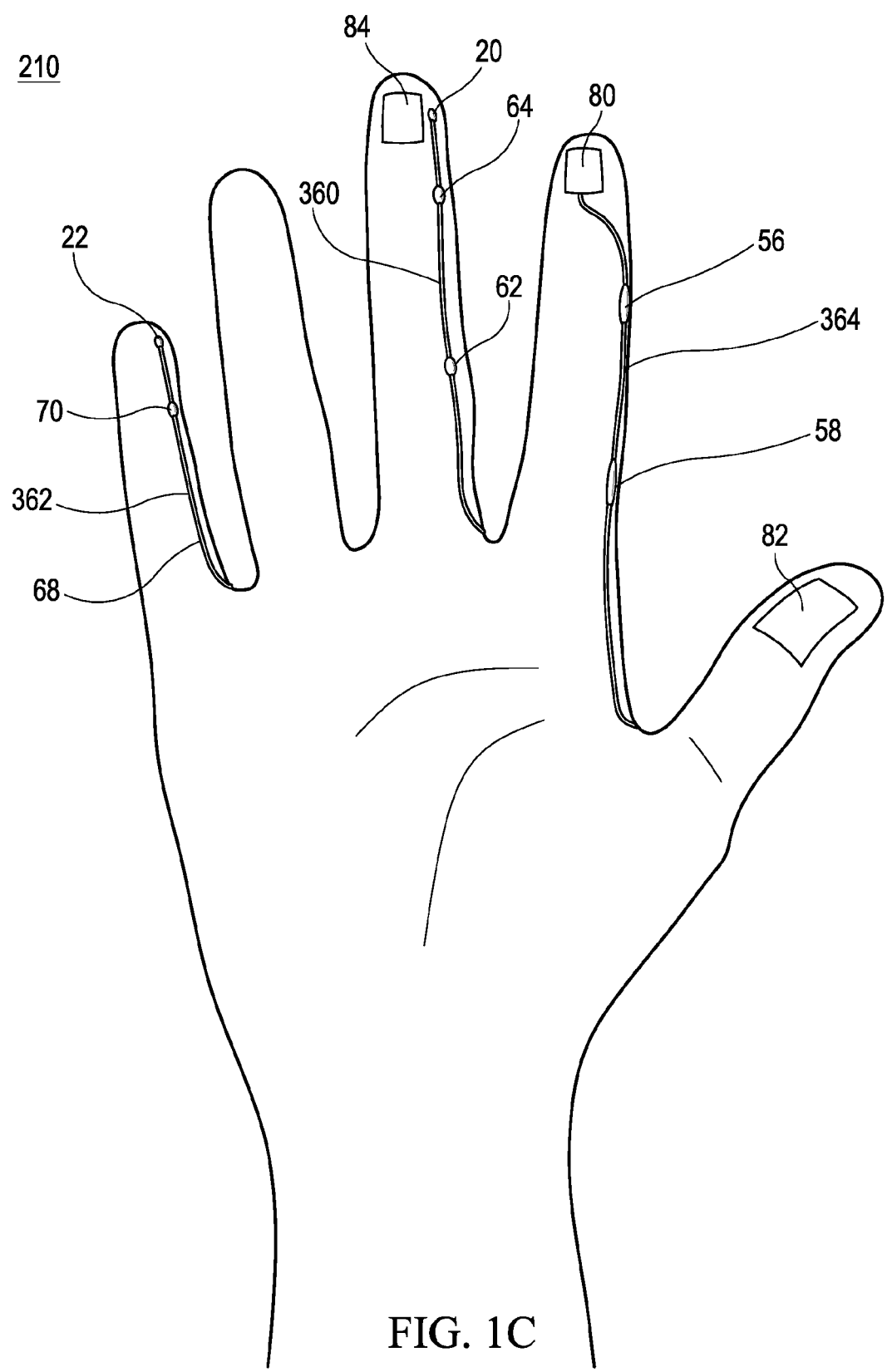
FIG. 1C is a volar view of the same former loaded with both surgical instruments and discrete elements.
Figure 2B:
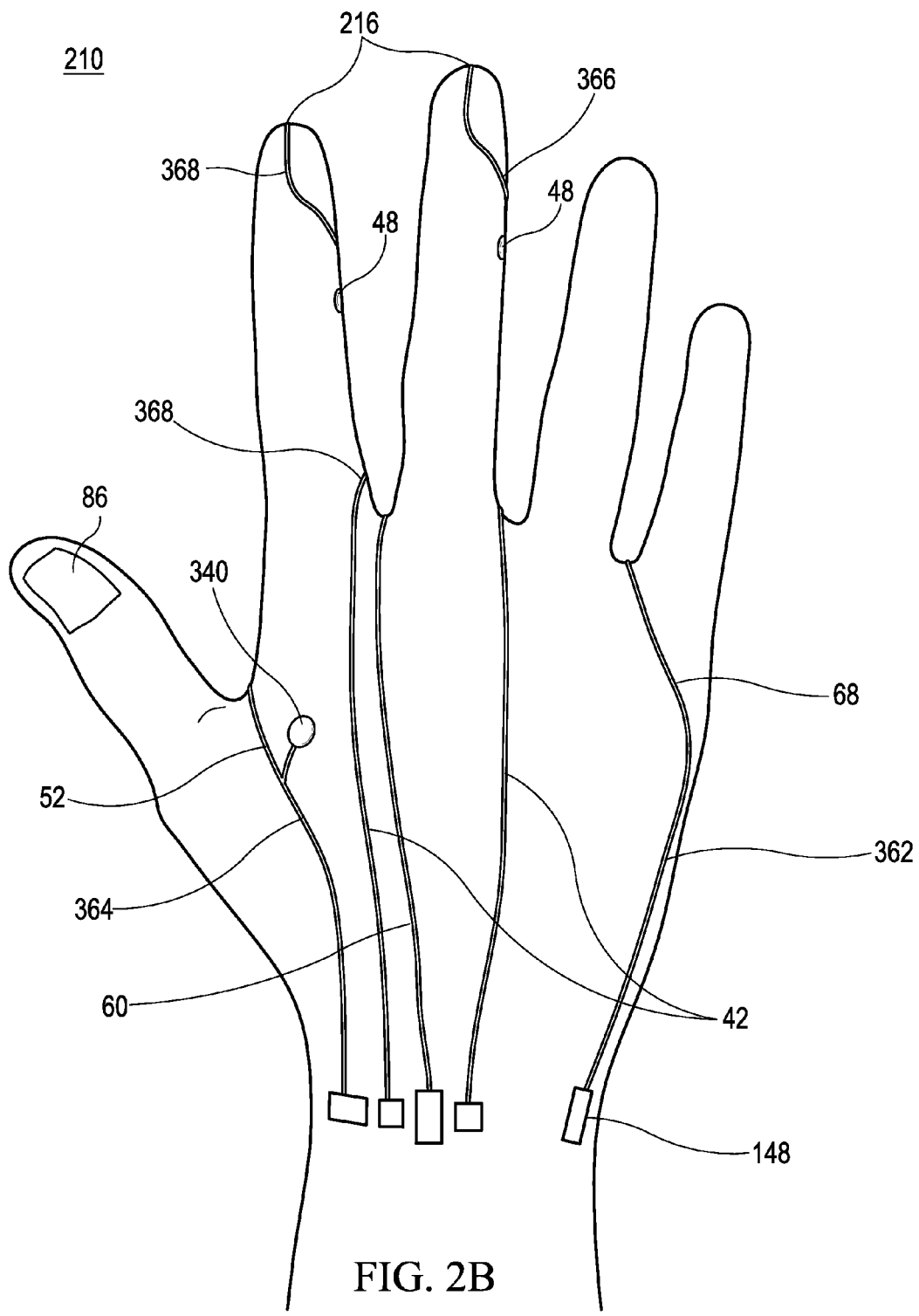
FIG. 2B is a dorsal view of the same former loaded with surgical systems and discrete elements.
Figure 3A:
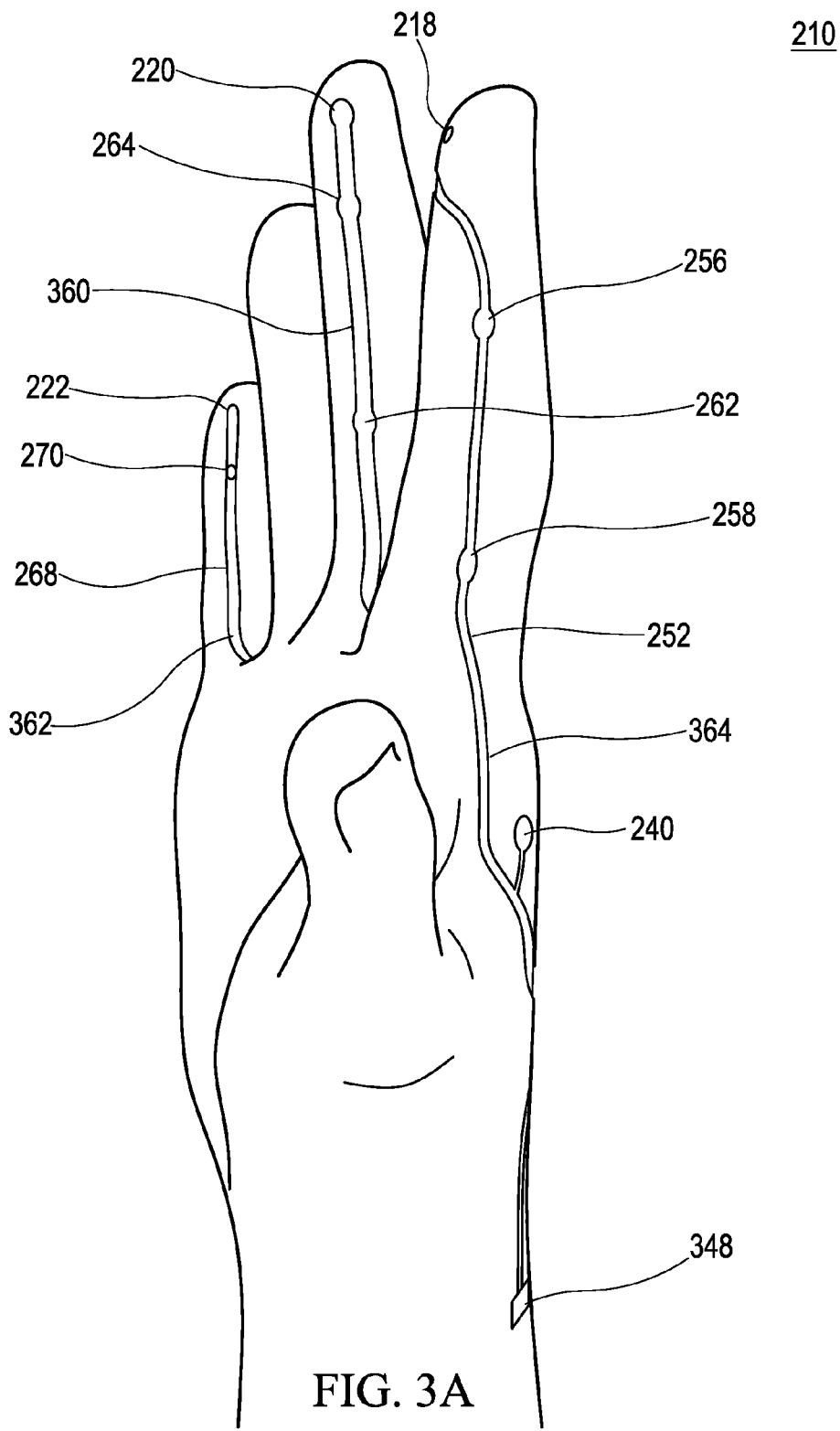
FIG. 3A is a side view of the former of FIG. 1.
Figure 3B:
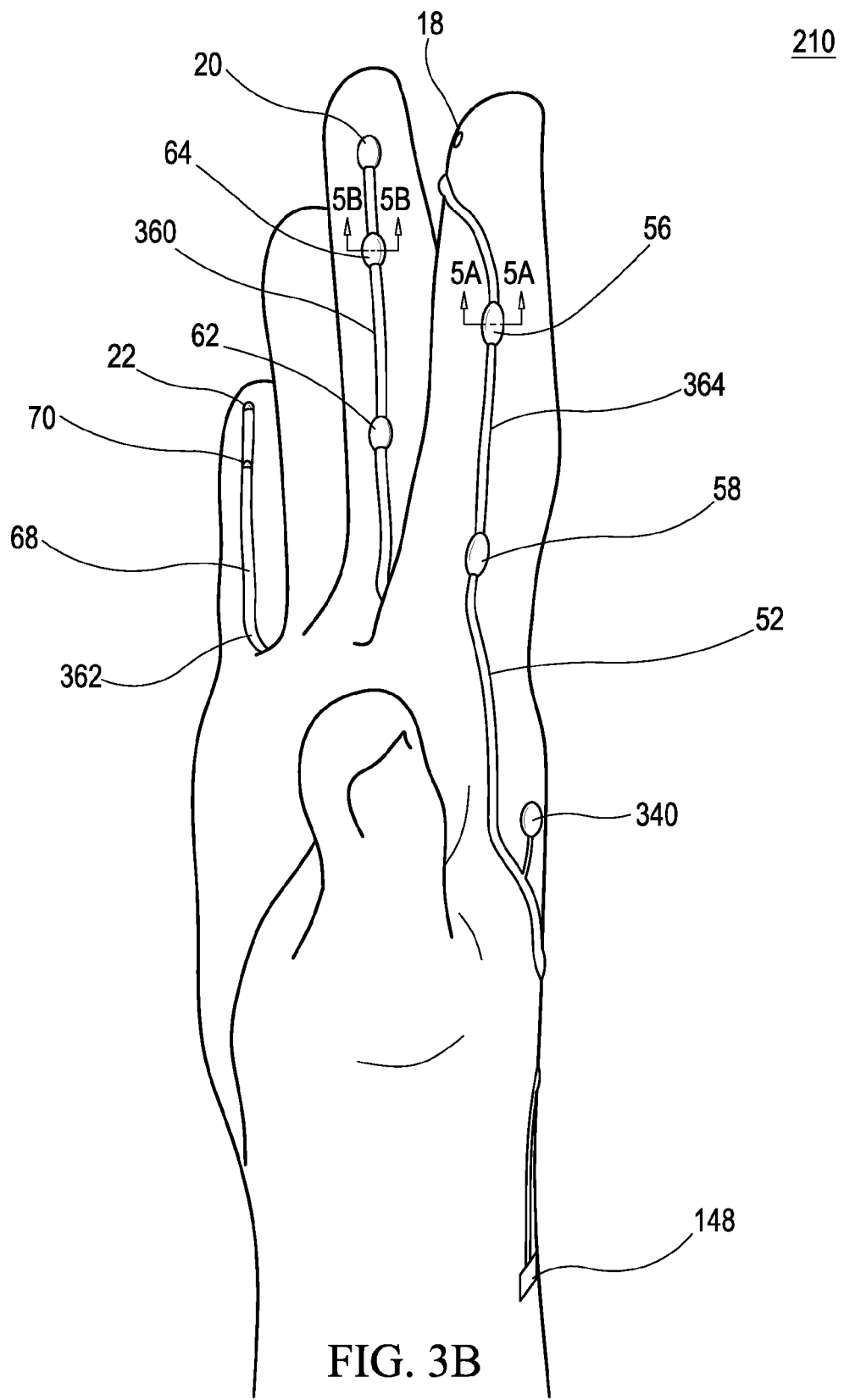
FIG. 3B is a side view of the same former loaded with surgical systems.

The former 210 can also include an irrigation system depression 362. As shown in the volar view of FIG. 1, the irrigation system depression 362 can include an irrigation device receiving portion 222, an irrigation control switch receiving portion 270, and an irrigation conduit receiving portion 268. As shown in the dorsal view of FIGS. 2A and 2B, the irrigation system depression 362 can include a terminal connector receiving portion 348 proximate a wrist portion of the former 210. The irrigation system depression 362 can start proximate a distal end of the little finger and extend along volar aspects, radial aspects or volar-radial aspects of the little finger. As shown in FIG. 2, the irrigation system depression 362 can then continue to a dorsal side of the former 210 between the ring finger and the little finger of the former and extend between or proximate the fourth and fifth metacarpals (e.g., along an ulnar portion of the fourth or fifth metacarpal).

The former 210 can also include a cutting system depression 364. As shown in the volar view of FIG. 1, the cutting system depression 364 can include a cutting device receiving portion 218, a cutting switch receiving portion 256, a coagulation switch receiving portion 258, and a cutting conduit receiving portion 252. As shown in the dorsal view of FIG. 2, the cutting system depression 364 can include a terminal connector receiving portion 348 proximate a wrist portion of the former 210. The cutting system depression 364 can start proximate a volar aspect of the distal end of the index finger and extend along radial aspects of the index finger. As shown in FIG. 2, the cutting system depression 364 can then continue to a dorsal side of the former 210 between the thumb and index finger of the former and extend between or proximate the first and second metacarpals (e.g., along a radial portion of the second metacarpal).

An exemplary interference fit is shown in FIG. 5A, which shows a cross-section of the relative positioning of the cutting switch 56 and cutting switch receiving portion 256, where the cutting switch 56 is a depression actuated switch. The cutting switch 56 can include a base 156 and a switch (e.g., button) 157 extending from the base 156, where the base 156 is wider than the switch 157. Similarly, the cutting switch receiving portion 256 can be tiered to include a base receiving portion 356 and a switch receiving portion 357 that extends deeper into the former 210 than the base receiving portion 356. The width of the base receiving portion 356 can be greater than the base 156 so that the coating precursor material can flow between the base 156 and the base receiving portion 356 when the former 210 is dipped into the coating precursor. However, the width of the switch receiving portion 357 and the switch 157 can be substantially identical so that there is contact between the sides of the switch 157 and the switch receiving portion 357 sufficient to prevent the coating precursor from flowing between the sides, i.e., sufficient to form an interference fit. The depth of the switch receiving portion 357 relative to the switch 157 can be selected to allow coating precursor to flow between lateral faces 158, 258 of the base 156 and base receiving portion 256, as shown in FIG. 5A, or to form an interference fit between the lateral faces 158, 258. Of course, this interference fit configuration can apply to any of the switches—especially depression actuated switches—described herein (e.g., 48, 56, 58, 62, 64, 70) or envisioned for use with the methods and systems described herein.

The former 210 can also include one or more light source system depressions 366, 368. As shown in the dorsal view of FIG. 2, the light source system depressions 366, 368 can include light source receiving portions 216, light source switch receiving portions 248, and a light source conduit receiving portions 242. As shown in the dorsal view of FIG. 2, the light source system depressions 364 can include a terminal connector receiving portion 348 proximate a wrist portion of the former 210.

The first light source system depression 366 can start proximate a distal end of a dorsal or distal aspect of the long finger and extend to an ulnar aspects of the long finger. As shown in FIG. 2, the first light source system depression 366 can then continue to a dorsal side of the former 210 between the long finger and ring finger of the former and extend between or proximate the third and fourth metacarpals (e.g., along an ulnar portion of the third metacarpal).

Similarly, the second light source system depression 368 can start proximate a distal end of a dorsal or distal aspect of the index finger and extend to an ulnar aspects of the index finger. As shown in FIG. 2, the first light source system depression 368 can then continue to a dorsal side of the former 210 between the index finger and long finger of the former and extend between or proximate the second and third metacarpals (e.g., along an ulnar portion of the second metacarpal).

The former 210 can also include one or more discrete element depressions (e.g., 280, 282, 284, 286, 288, 290). As shown in the volar view of FIG. 1, a heat shield depression 280 can be positioned at a distal end of an index finger of the former 210. The heat shield depression 280 can overlap with a portion of the cutting device receiving portion 218 of the cutting system depression 364. The heat shield depression 280 can be generally rectangular or any other appropriate shape for use in connection with the cutting device. The cutting device receiving portion 218 will generally extend deeper than the heat shield depression 280 so that the cutting device 18 can be loaded, as shown in FIG. 1B, and then covered by the heat shield 80, as shown in FIG. 1C. Alternately, the heat shield 80 and cutting device 18 can be a single element. In order to simplify the Figures, discrete element depressions 280, 282 and 284 are only shown in FIG. 1.

The former 210 can include at least one reinforcing element depression 282, 286. As shown in FIG. 1, a reinforcing element depression 282 can be positioned at a distal end of a volar aspect of the thumb of the former 210. As shown in FIG. 2, a reinforcing element depression 286 can be positioned at a distal end of a dorsal aspect of the thumb of the former 210. These locations of the thumb may be reinforced in order to reduce wear when these locations are used to actuate switches embedded in, or protruding from, the glove. As will be understood, reinforcing elements can be positioned on any portion of the former 210 where it would be desired to reinforce the glove, including any aspect of the fingers and the volar or dorsal metatarsal region of the hand. The reinforcing element depression(s) can be generally rectangular or any other appropriate shape corresponding to the area where reinforcement in desired. In order to simplify the Figures, reinforcing elements 282, 286 are only shown in FIGS. 1 and 2, respectively.

The former 210 can include additional discrete element depressions, such as a thermometer strip depression 284. The corresponding thermometer strip can visually indicate temperature for example by color. As shown in FIG. 1, a thermometer strip depression 284 can be positioned at a distal end of a volar aspect of the long finger of the former 210. The thermometer strip depression 284 can be generally rectangular or any other appropriate shape corresponding to the area where reinforcement in desired. In order to simplify the Figures, thermometer strip depression 284 is only shown in FIG. 1.

Figure 4A:
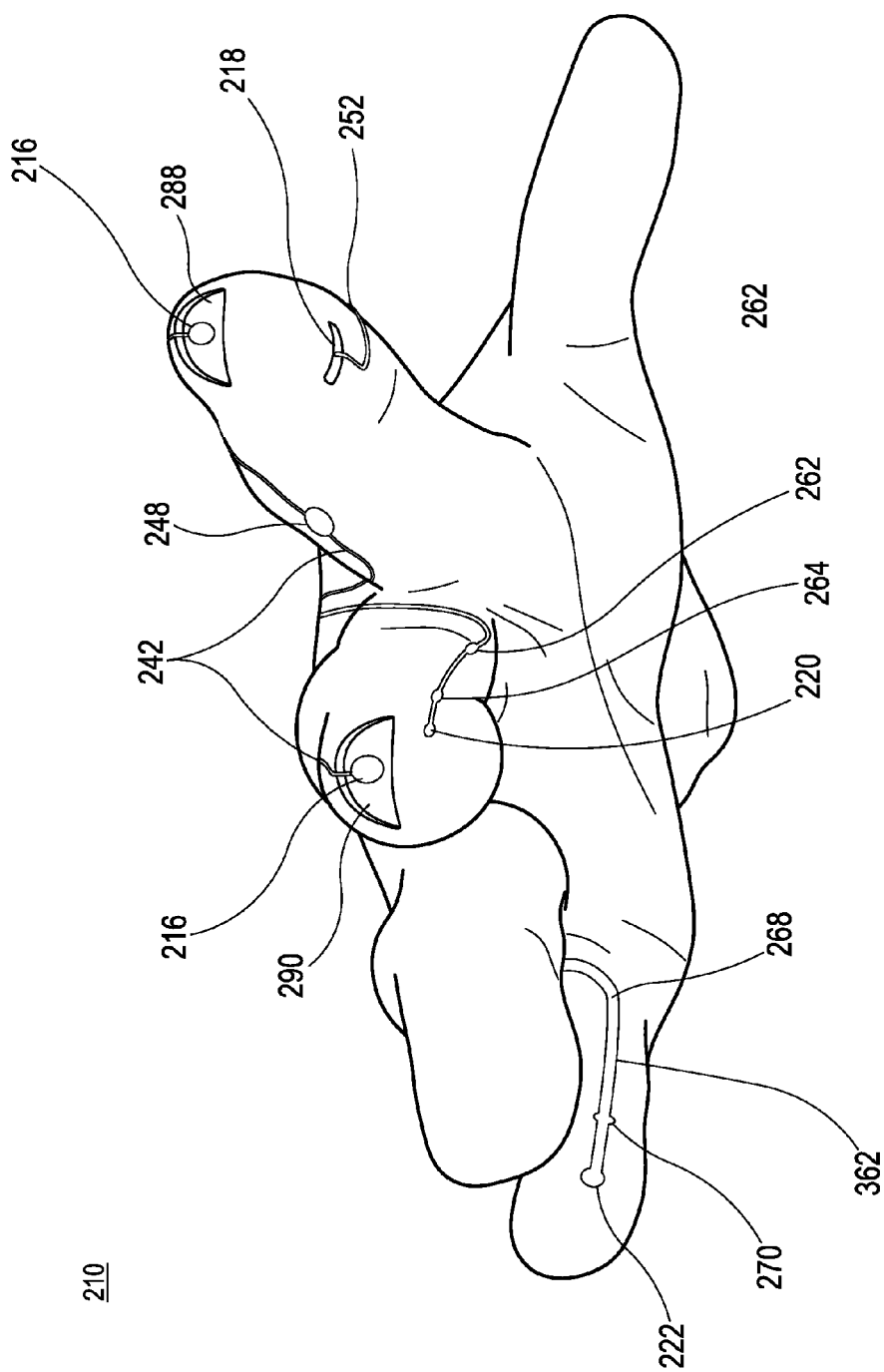
FIG. 4A is an end view of the former of FIG. 1.
Figure 4B:
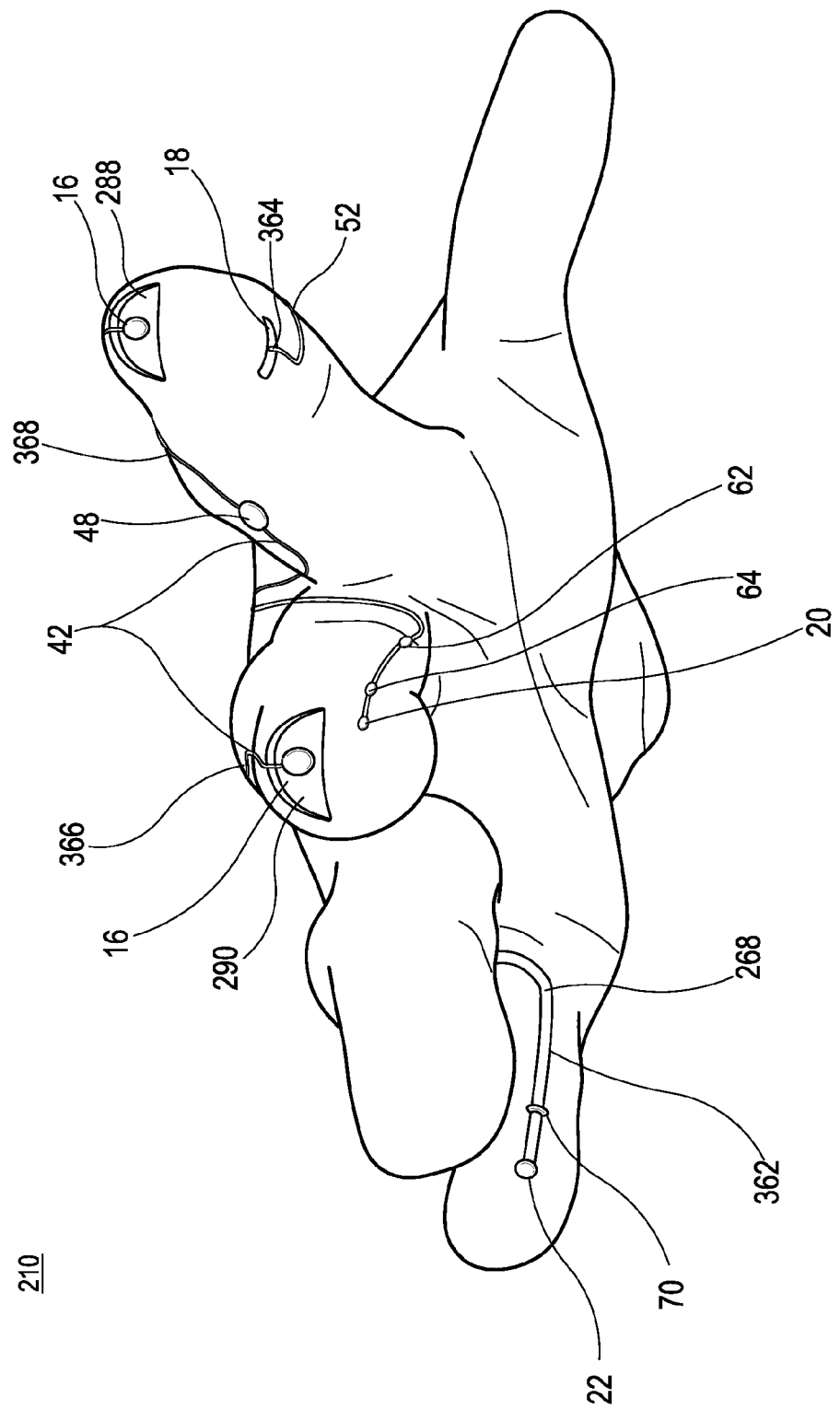
FIG. 4B is an end view of the same former loaded with surgical systems.
Figure 4C:
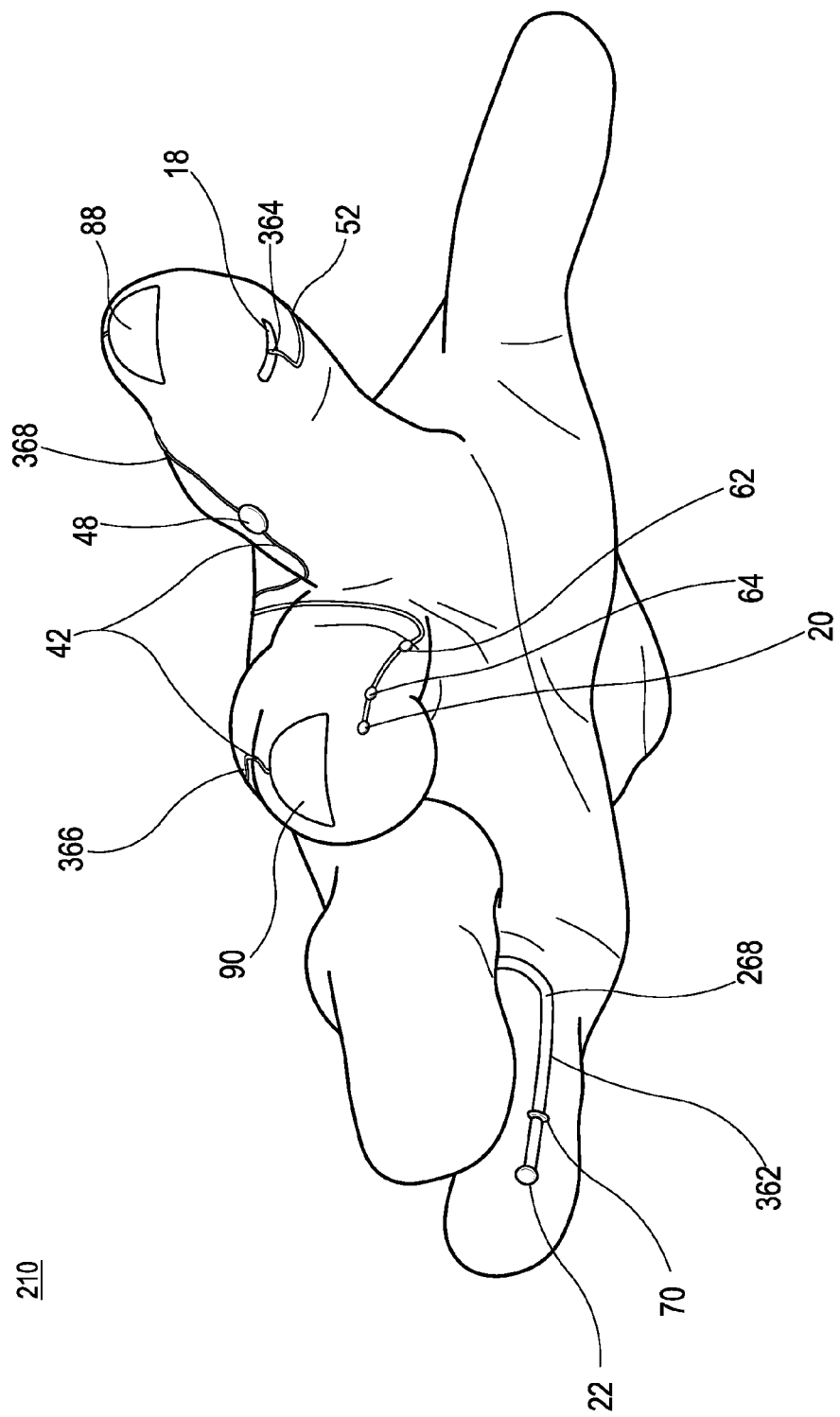
FIG. 4C is an end view of the same former loaded with both surgical instruments and discrete elements.

As shown in the end view of FIG. 4, at least one reflective element depression 288, 290 can be positioned proximate light source receiving portions 216. As shown in FIG. 4, a first reflective element depressions 288 can be positioned at a distal end of the index finger and a second reflective element depressions 290 can be positioned as a distal end of the long finger. The reflective element depressions 288, 290 can overlap with a portion of the light source receiving portions 216. The reflective element depressions 288, 290 can be any shape helpful for directing light emitted from the light sources in a volar-distal direction. The light source receiving portion(s) 216 will generally extend deeper than the corresponding reflective element depression(s) 288, 290 so that the light source 16 can be loaded, as shown in FIG. 4B, and then covered by the reflective element 88, 90, as shown in FIG. 4C. Alternately, the reflective element 88 or 90 and light source 16 can be a single element. In order to simplify the Figures, reflective element depressions 288, 290 are only shown in FIG. 4.

The depths and fit of the depressions can be varied in order to leave appropriate portions of the surgical systems 14 exposed after application of the coating and other portions completely embedded in the glove. For example, a loose fit may be desired around the conduits so that they are completely embedded in the polymer forming the glove 12. In contrast, an interference fit between portions of a depression and portions of a surgical system may be utilized in order to have certain portions exposed, e.g., switches, ports and interconnects.

In some methods, the former 210 may be dipped only up to the wrist in order to ensure that the proximal portions of the conduits (e.g., 42, 52, 60 and 68) and the terminal connector 148 are exposed. For example, as shown in FIG. 2A, the former 210 may be dipped fingers first up to the wrist (line D) into a pool of coating precursor. Thus, the proximal portions of a conduit and the terminal connector 148 would be exposed. Alternately, the method could include removing portions of the glove in order to ensure that specific portions of the surgical systems 14 are exposed.

It is known to use formers in the production of elastomeric gloves. These conventional formers are shaped similarly to the human hand and do not include depressions, especially depressions adapted to receive surgical systems and discrete elements such as those described herein. Thus, attachment of surgical systems to conventional elastomeric gloves would require post-formation attachment of the surgical system to the elastomeric gloves, which is inefficient and risks the integrity of the barrier function of the gloves. The claimed method and formers are a significant improvement over the conventional techniques. Accordingly, the invention is also drawn to the formers described herein for use in the methods described herein.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A method of making a surgical glove, comprising:
   providing a first surgical system comprising a first surgical instrument, and a first switch for controlling the first surgical system;
   providing a former comprising a hand-shaped portion, the former comprising a first depression for receiving the first surgical system;
   loading the first surgical system into the first depression to produce a loaded former; and
   applying a polymer coating over the hand-shaped portion of the loaded former to form a surgical glove, wherein at least a portion of the first surgical system is embedded within the surgical glove.

2. The method according to claim 1, wherein the first depression is adapted to produce an interference fit with at least a portion of the first surgical system.

3. The method according to claim 2, wherein said interference fit is formed with a portion of one or more of said first surgical instrument, said first switch and said proximal interconnection.

4. The method according to claim 1, wherein said applying step comprises dipping said loaded former into a pool of coating precursor.

5. The method according to claim 1, wherein said first depression comprises a first surgical instrument receiving portion and a first switch receiving portion.

6. The method according to claim 1, wherein said first surgical system further comprises a first conduit.

7. The method according to claim 6, wherein said first depression comprises a first surgical instrument receiving portion, a first conduit receiving portion, and a first switch receiving portion.

8. The method according to claim 1, wherein the interference fit is formed with a portion of said first surgical instrument, a portion of said first switch, or both.

9. The method according to claim 1, wherein said first surgical system further comprises a proximal interconnection.

10. The method according to claim 1, further comprising removing the surgical glove from the former by turning the surgical glove inside-out.

11. The method according to claim 1, wherein a portion of said first surgical system is embedded within the surgical glove and another portion of said first surgical system is exposed.

12. The method according to claim 11, wherein the exposed portion comprises a portion of said first surgical instrument, a portion of said first switch, or both.

13. The method according to claim 11, wherein the exposed portion corresponds to the portion of the first surgical system producing an interference fit with the first depression.

14. The method according to claim 1, further comprising:
   providing a second surgical system comprising a second surgical instrument and a second switch for controlling the second surgical system, wherein said former further comprises a second depression for receiving said second surgical system, and said second depression is adapted to produce a second interference fit with at least a portion of the second surgical system; and
   loading said second surgical system into said second depression.

15. The method according to claim 14, wherein the first depression comprises a first surgical instrument receiving portion and a first switch receiving portion, and the second depression comprises a second surgical instrument receiving portion and a second switch receiving portion.

16. The method according to claim 14, wherein the first surgical system further comprises a first conduit, and the second surgical system further comprises a second conduit.

17. The method according to claim 16, wherein the first depression comprises a first surgical instrument receiving portion, a first conduit receiving portion, and a first switch receiving portion, and the second depression comprises a second surgical instrument receiving portion, a second conduit receiving portion, and a second switch receiving portion.

18. The method according to claim 16, wherein the first and second conduit receiving portions do not intersect.

19. The method according to claim 14, wherein an interference fit is formed with a portion of said first surgical instrument, a portion of said first switch, or both, and a second interference fit is formed with a portion of said second surgical instrument, a portion of said second switch, or both.

20. The method according to claim 14, wherein the first and second surgical systems further comprise first and second proximal interconnections, respectively.

21. The method according to claim 20, wherein an interference fit is formed with a portion of at least one of said first surgical instrument, said first switch and said first proximal interconnection, and a second interference fit is formed with a portion of at least one of said second surgical instrument, said second switch and said second proximal interconnection.

22. The method according to claim 14, wherein a portion of said first surgical system is embedded within the surgical glove and another portion of said first surgical system is exposed, and wherein a portion of said second surgical system is embedded within the surgical glove and another portion of said second surgical system is exposed.

23. The method according to claim 22, wherein the exposed portion of said first surgical system comprises a portion of said first surgical instrument, a portion of said first switch or both, and the exposed portion of said second surgical system comprises a portion of said second surgical instrument, a portion of said second switch or both.

24. The method according to claim 1, wherein the surgical glove comprises:
   a first and second surgical system attached to the surgical glove, wherein the first surgical system comprises a first surgical instrument and a first conduit, wherein the second surgical system comprises a second surgical instrument and a second conduit, wherein each of the first and second surgical systems are attached to an index finger, a long finger or a little finger of the surgical glove;
   a first switch attached to the surgical glove for controlling the first surgical system, said first switch attached to a finger of the surgical glove to which the first surgical system is attached;
   a second switch attached to the surgical glove for controlling the second surgical system, said second switch attached to a finger of the surgical glove to which the second surgical system is attached, and wherein the first and second switches are operable by a thumb of a human hand wearing the surgical glove.

25. The method according to claim 1, wherein the former further comprises a first discrete element depression.

26. The method according to claim 25, wherein the first depression comprises a first surgical instrument receiving portion, and the first discrete element depression and the first surgical instrument receiving portion overlap.

27. A method of making a polymeric glove, comprising:
providing a first functional component, wherein said first functional component is selected from a first discrete element and a first component system coupled to a first conduit;
providing a former comprising an appendage-shaped portion, the former comprising a first depression for receiving the first functional component;
loading the first functional component into the first depression to produce a loaded former; and
applying a polymer coating over the appendage-shaped portion of the loaded former to form an polymeric glove, wherein at least a portion of the first functional component is embedded within the polymeric glove.

28. The method according to claim 27, wherein said first depression is adapted to produce an interference fit with at least a portion of said first functional component.

29. The method according to claim 28, wherein a portion of the first functional component is embedded within the polymeric glove and another portion of the first functional component is exposed.

30. The method according to claim 27, wherein:
said first functional component is a first component system comprising a first active end and a first conduit;
said first depression comprises a first active end receiving portion and a first conduit receiving portion; and
said loading step comprises loading said first active end into said first active end receiving portion and said first conduit into said first conduit receiving portion.

31. The method according to claim 27, wherein said first functional component is a first discrete element.

32. The method according to claim 27, further comprising:
providing a second functional component, wherein said second functional component is selected from a second discrete element and a second component system coupled to a second conduit, wherein said former further comprises a second depression for receiving a second functional component; and
loading the second functional component into the second depression.

33. The method according to claim 27, wherein said first functional component is a first discrete element, and the first discrete element is embedded in a distal portion of a thumb of the glove.

34. A method of making a polymeric glove, comprising:
providing a first functional component, wherein said first functional component is selected from a first discrete element and a first component system coupled to a first conduit;
providing a former comprising an appendage-shaped portion;
applying a first polymer coating over the appendage-shaped portion of the former to form a first glove layer;
loading the first functional component over the first glove layer to produce a loaded former; and
applying a second polymer coating over the appendage-shaped portion of the loaded former to form a second glove layer, wherein the first and second glove layers form a polymeric glove, and wherein at least a portion of the first functional component is embedded within the polymeric glove.

* * * * *